(12) United States Patent
Hamill

(10) Patent No.: US 7,771,975 B2
(45) Date of Patent: Aug. 10, 2010

(54) POLYNUCLEOTIDE ANALYSIS USING COMBINATORIAL PCR

(75) Inventor: Brendan James Hamill, Milnathort (GB)

(73) Assignee: Point-2-Point Genomics Limited, Edinburgh (GB)

( * ) Notice: Subject to any disclaimer, the term of this patent is extended or adjusted under 35 U.S.C. 154(b) by 1586 days.

(21) Appl. No.: 10/473,796

(22) PCT Filed: Mar. 28, 2002

(86) PCT No.: PCT/GB02/01489

§ 371 (c)(1),
(2), (4) Date: Sep. 30, 2003

(87) PCT Pub. No.: WO02/081743

PCT Pub. Date: Oct. 17, 2002

(65) Prior Publication Data

US 2004/0132040 A1    Jul. 8, 2004

(30) Foreign Application Priority Data

Apr. 2, 2001    (GB) ................................ 0108182.7

(51) Int. Cl.
*C12P 19/34*    (2006.01)
*C12Q 1/68*    (2006.01)
(52) U.S. Cl. .......................................... 435/91.2; 435/6
(58) Field of Classification Search ....................... None
See application file for complete search history.

(56) References Cited

U.S. PATENT DOCUMENTS

| 5,922,574 | A | 7/1999 | Minter |
| 6,017,738 | A | 1/2000 | Morris et al. |
| 6,103,463 | A | 8/2000 | Chetverin et al. |
| 6,355,431 | B1 * | 3/2002 | Chee et al. ....................... 435/6 |

FOREIGN PATENT DOCUMENTS

| EP |  | 731176 A2 * | 9/1996 |
| WO | WO 93/04199 |  | 3/1993 |
| WO | WO 96/26291 |  | 8/1996 |
| WO | WO 98/28438 |  | 7/1998 |
| WO | WO 93/17126 |  | 9/1998 |
| WO | WO 98/44151 |  | 10/1998 |
| WO | WO 99/10538 |  | 3/1999 |
| WO | WO 99/36567 |  | 7/1999 |
| WO | WO 00/47767 |  | 8/2000 |
| WO | WO 00/60919 |  | 10/2000 |
| WO | WO 01/34842 A2 |  | 5/2001 |
| WO | WO 01/48242 A2 |  | 7/2001 |
| WO | WO 0148242 A2 * | 7/2001 |

OTHER PUBLICATIONS

Strizhkov et al. (2000) PCR amplification on a microarray of gel-immobilized oligonucleotides: detection of bacterial toxin- and drug-resistant genes and their mutations. Biotechniques. vol. 29. pp. 844-846, 848, 850-852, 854, 856-857 (10 pages total).*
Tettelin et al. Optimized multiplex PCR: efficiently closing a whole-genome shotgun sequencing project. Genomics (1999) 62: 500-507.*
Nerenberg et al., Publication No. US 2001/0014449 A1, "Methods for Determination of Single Nucleic Acid Polymorphisms Using Bioelectronic Microchip," Aug. 16, 2001.
Syvanen et al., "A Primer-Guided Nucleotide Incorporation Assay in the Genotyping of Apolipoprotein E," Genomics 8:684-692 (1990).
Huber et al., "Detection of Single Base Alterations in Genomic DNA by Solid Phase Polymerase Chain Reaction on Oligonucleotide Microarrays," Analytical Biochemistry 299:24-30 (2001).

* cited by examiner

*Primary Examiner*—Kenneth R. Horlick
*Assistant Examiner*—Angela M Bertagna
(74) *Attorney, Agent, or Firm*—Ropes & Gray LLP

(57) ABSTRACT

The invention comprises a two-step process for analysis of polynucleotides by chain extension of multiple polynucleotide primers attached to solid supports by first performing PCR of the samples in the presence of multiple oligonucleotides in solution, the oligonucleotides of both sets being similar or identical. This produces immobilized single-strand polynucleotides containing genetic sequence data derived from sample molecules. In a second step, support-bound polynucleotides are interrogated by hybridization with a single labeled oligonucleotide probe or by second-strand synthesis with a primer-dependent polymerase using an oligonucleotide primer and nucleotide monomers, in which either or both of the primer and nucleotide monomers are labeled. Incorporation of label demonstrates the presence of two separate defined-sequence primers within the sample polynucleotide. The presence or absence within the sample of the multiple combinations of primers is demonstrable in a single experiment by use of suitable apparatus, such as an oligonucleotide array.

12 Claims, 13 Drawing Sheets

| Sequence | SEQ ID | Sequence | SEQ ID | Sequence | SEQ ID | Sequence | SEQ ID |
|---|---|---|---|---|---|---|---|
| GTTTCGCTCC | (SEQ ID NO:1) | TGCTCTGCCC | (SEQ ID NO:51) | GTAGACCCGT | (SEQ ID NO:101) | TTTGCCCGGA | (SEQ ID NO:151) |
| TGATCCCTGG | (SEQ ID NO:2) | GGTGACGCAG | (SEQ ID NO:52) | CCTTGACGCA | (SEQ ID NO:102) | AGGGAACGAG | (SEQ ID NO:152) |
| CATCCCCCTG | (SEQ ID NO:3) | GTCCACACGG | (SEQ ID NO:53) | TTCCCCCGCT | (SEQ ID NO:103) | CCACAGCAGT | (SEQ ID NO:153) |
| GGACTGGAGT | (SEQ ID NO:4) | TGGGGGACTC | (SEQ ID NO:54) | TCCGCTCTGG | (SEQ ID NO:104) | ACCCCCGAAG | (SEQ ID NO:154) |
| TGCGCCCTTC | (SEQ ID NO:5) | CTGCTGGGAC | (SEQ ID NO:55) | GGAGGGTGTT | (SEQ ID NO:105) | GGACCCTTAC | (SEQ ID NO:155) |
| CCCAAGGTCC | (SEQ ID NO:6) | AAGACCCCTC | (SEQ ID NO:56) | GAGTCTCAGG | (SEQ ID NO:106) | GGTGACTGTG | (SEQ ID NO:156) |
| GGTGCGGGAA | (SEQ ID NO:7) | AGATGCAGCC | (SEQ ID NO:57) | TTATCGCCCC | (SEQ ID NO:107) | CTACTGCCGT | (SEQ ID NO:157) |
| CCAGATGCAC | (SEQ ID NO:8) | TCACCACGGT | (SEQ ID NO:58) | CCCGATTCGG | (SEQ ID NO:108) | GGACTGCAGA | (SEQ ID NO:158) |
| GTGACATGCC | (SEQ ID NO:9) | CTTCACCCGA | (SEQ ID NO:59) | TGCGGCTGAG | (SEQ ID NO:109) | ACGGCGTATG | (SEQ ID NO:159) |
| TCAGGGAGGT | (SEQ ID NO:10) | CACCAGGTGA | (SEQ ID NO:60) | ACGCACAACC | (SEQ ID NO:110) | AACGGTGACC | (SEQ ID NO:160) |
| CCCGGCATAA | (SEQ ID NO:11) | TCGTTCCGCA | (SEQ ID NO:61) | ACTCCTGCGA | (SEQ ID NO:111) | CTGCTTAGGG | (SEQ ID NO:161) |
| CCCGTTGGGA | (SEQ ID NO:12) | CCTCTCGACA | (SEQ ID NO:62) | GTCCCGTGGT | (SEQ ID NO:112) | ACGCCAGTTC | (SEQ ID NO:162) |
| TCTCCGCTTG | (SEQ ID NO:13) | CATACCGTGG | (SEQ ID NO:63) | CCACACTACC | (SEQ ID NO:113) | TGGTCGCAGA | (SEQ ID NO:163) |
| CCGAACACGG | (SEQ ID NO:14) | TGAGCCTCAC | (SEQ ID NO:64) | CACCCGGATC | (SEQ ID NO:114) | GGACACCACT | (SEQ ID NO:164) |
| CTCCATGGGG | (SEQ ID NO:15) | AAGCCCGAGG | (SEQ ID NO:65) | TGTAGCAGGG | (SEQ ID NO:115) | AAGCGGCCTC | (SEQ ID NO:165) |
| GGCACGTAAG | (SEQ ID NO:16) | CCACGGGAAG | (SEQ ID NO:66) | GACAGGAGGT | (SEQ ID NO:116) | TCGGCGGTTC | (SEQ ID NO:166) |
| ACGTAGCGTC | (SEQ ID NO:17) | CAGCACTGAC | (SEQ ID NO:67) | CAGTGCTGTG | (SEQ ID NO:117) | GGCTTATGCC | (SEQ ID NO:167) |
| CTGTTGCTAC | (SEQ ID NO:18) | CCTCCAGTGT | (SEQ ID NO:68) | GTCAGAGTCC | (SEQ ID NO:118) | CTCGCTATCC | (SEQ ID NO:168) |
| AAGTCCGCTC | (SEQ ID NO:19) | TCCCACGCAA | (SEQ ID NO:69) | AGCATGGCTC | (SEQ ID NO:119) | GGTGCACGTT | (SEQ ID NO:169) |
| CCCAGTCACT | (SEQ ID NO:20) | TCAGAGCGCC | (SEQ ID NO:70) | TGGCGTCCTT | (SEQ ID NO:120) | ACACACGCTG | (SEQ ID NO:170) |
| GGGCCACTCA | (SEQ ID NO:21) | CAAGGGCAGA | (SEQ ID NO:71) | TTCCCCGCGA | (SEQ ID NO:121) | GGTGAACGCT | (SEQ ID NO:171) |
| GGAGAGACTC | (SEQ ID NO:22) | GGCAGGCTGT | (SEQ ID NO:72) | GGGTGTGTAG | (SEQ ID NO:122) | CCAACGTCGT | (SEQ ID NO:172) |
| TCCACTCCTG | (SEQ ID NO:23) | AACGGCGACA | (SEQ ID NO:73) | AGGATGCCAG | (SEQ ID NO:123) | GATGCCAGAC | (SEQ ID NO:173) |
| CACAGAGGGA | (SEQ ID NO:24) | CACCCCTGAG | (SEQ ID NO:74) | AATGCGCCAG | (SEQ ID NO:124) | GTCCGTATGG | (SEQ ID NO:174) |
| GGGTTTGGCA | (SEQ ID NO:25) | CCTTCGGAAG | (SEQ ID NO:75) | GGATGCCACT | (SEQ ID NO:125) | GACCAATGCC | (SEQ ID NO:175) |
| GTGGCATCTC | (SEQ ID NO:26) | AAGGCTCACC | (SEQ ID NO:76) | AGACGATGGG | (SEQ ID NO:126) | GGGGCCAATGT | (SEQ ID NO:176) |
| CATCGCCGCA | (SEQ ID NO:27) | AGAGCCGTCA | (SEQ ID NO:77) | AAGCCTGCGA | (SEQ ID NO:127) | GACGTGGTGA | (SEQ ID NO:177) |
| ACAGCCTGCT | (SEQ ID NO:28) | AGGCAGAGCA | (SEQ ID NO:78) | GGGTCTCGGT | (SEQ ID NO:128) | GTGGAGTCAG | (SEQ ID NO:178) |
| GGCTGCAATC | (SEQ ID NO:29) | AGCAGCGCAC | (SEQ ID NO:79) | GGTCGATCTG | (SEQ ID NO:129) | TGAGGGTCCC | (SEQ ID NO:179) |
| GGCTGCGACA | (SEQ ID NO:30) | CAAACGTGGG | (SEQ ID NO:80) | AGTCGCCCTT | (SEQ ID NO:130) | AGCCGTGGAA | (SEQ ID NO:180) |
| CAAAGGGCGG | (SEQ ID NO:31) | AAGTGCACGG | (SEQ ID NO:81) | CAATCGGGTC | (SEQ ID NO:131) | AACGGGCGTC | (SEQ ID NO:181) |
| CTGAACCGCT | (SEQ ID NO:32) | CCCTACTGGT | (SEQ ID NO:82) | AAGAGGGCGT | (SEQ ID NO:132) | GGCAAACCCT | (SEQ ID NO:182) |
| TCTCGCCTAC | (SEQ ID NO:33) | GGCAGGCAAG | (SEQ ID NO:83) | GGTTCCTCTG | (SEQ ID NO:133) | ACGAGAGGCA | (SEQ ID NO:183) |
| GTAGGCCTCA | (SEQ ID NO:34) | TCGCTTCTCC | (SEQ ID NO:84) | GAACGAGGGT | (SEQ ID NO:134) | CTTGGCACGA | (SEQ ID NO:184) |
| ACCGCATGGG | (SEQ ID NO:35) | AAGAGGCCAG | (SEQ ID NO:85) | TTTGCCCCGT | (SEQ ID NO:135) | TCTTCGGAGG | (SEQ ID NO:185) |
| GGCATCGGCT | (SEQ ID NO:36) | TGCCGCACTT | (SEQ ID NO:86) | ACGGCGATGA | (SEQ ID NO:136) | AAGGCACCAG | (SEQ ID NO:186) |
| AGCCGTTCAG | (SEQ ID NO:37) | ACGAGCATGG | (SEQ ID NO:87) | GACTCTAACC | (SEQ ID NO:137) | CCTCACGTCC | (SEQ ID NO:187) |
| GGGTCCAAAG | (SEQ ID NO:38) | AAGCCCCCCA | (SEQ ID NO:88) | ACGCTGCCAG | (SEQ ID NO:138) | TCGCGGAACC | (SEQ ID NO:188) |
| CTATCCTGCC | (SEQ ID NO:39) | TCGCTGGTGT | (SEQ ID NO:89) | TGGTGCACTC | (SEQ ID NO:139) | GGCAAAGCTG | (SEQ ID NO:189) |
| GTCGTAGCGG | (SEQ ID NO:40) | TCGGGCATCA | (SEQ ID NO:90) | GACACAGCCC | (SEQ ID NO:140) | CCTGTTCCCT | (SEQ ID NO:190) |
| ACTCCACGTC | (SEQ ID NO:41) | GGGAACCCGT | (SEQ ID NO:91) | GTCCATGCAG | (SEQ ID NO:141) | GTGTCGAGTC | (SEQ ID NO:191) |
| CACCGCAGTT | (SEQ ID NO:42) | TCGCTGCGGA | (SEQ ID NO:92) | AACGGCGGTC | (SEQ ID NO:142) | TCAGCACAGG | (SEQ ID NO:192) |
| AGCCAGGCTG | (SEQ ID NO:43) | AAGGCTGCTG | (SEQ ID NO:93) | CTTCCAGGAC | (SEQ ID NO:143) | TGTCCTGCGT | (SEQ ID NO:193) |
| GGCGTAAGTC | (SEQ ID NO:44) | GGGGGAGATG | (SEQ ID NO:94) | AGCCGGGTAA | (SEQ ID NO:144) | ACCACGCCTT | (SEQ ID NO:194) |
| GGGTGCAGTT | (SEQ ID NO:45) | CTGTGTGCTC | (SEQ ID NO:95) | TGATGCCGCT | (SEQ ID NO:145) | GAGTCCTCAC | (SEQ ID NO:195) |
| CACACCGTGT | (SEQ ID NO:46) | GGCGCGTTAG | (SEQ ID NO:96) | ACCGTGCCGT | (SEQ ID NO:146) | AACCCTTCCC | (SEQ ID NO:196) |
| GTCCTCGTGT | (SEQ ID NO:47) | GACGAGCAGG | (SEQ ID NO:97) | TGACCAGGCA | (SEQ ID NO:147) | AGTTCCGCGA | (SEQ ID NO:197) |
| ACGGTTCCAC | (SEQ ID NO:48) | GGCTGCCAGT | (SEQ ID NO:98) | CACGGACCGA | (SEQ ID NO:148) | GTTGCGCAGT | (SEQ ID NO:198) |
| GTCTTGGGCA | (SEQ ID NO:49) | TGGAGTCCCC | (SEQ ID NO:99) | TCGCAGCGTT | (SEQ ID NO:149) | TGACAGCCCC | (SEQ ID NO:199) |
| GTCACCTGCT | (SEQ ID NO:50) | CCCGTCTACC | (SEQ ID NO:100) | CTGCAATGGG | (SEQ ID NO:150) | TCTGCCTGGA | (SEQ ID NO:200) |

Figure 17

SEQUENCE X =
(5'-)AGTTCTTCCGTAGCTGATTCGATTCGATCGAGCTACGTTCGATCGATACGCTAGCTTAGCTTACTAACTTAGGATTAGTAGCTC SEQ ID NO:201
    ||||||||||||||||||||||||||||||||||||||||||||||||||||||||||||||||||||||||||||||||||||||
(3'-)TCAAGAAGGCATCGACTAAGCTAAGCTAGCTCGATGCAAGCTAGCTATGCGATCGATGCGAGTATGCCGGGATCGAATGATTGAATCCTAATCATCGAG SEQ ID NO:202

SEQUENCE Y =
(5'-)TGCCATACGAAGTTCAGCATGCTATCGTGTCTTAGCATCATAGTCTTCTAGCATACAGACTTTAGCTACGACGATGCATCCGACTAGCTTCTAGCTA SEQ ID NO:203
    ||||||||||||||||||||||||||||||||||||||||||||||||||||||||||||||||||||||||||||||||||||||
(3'-)ACGGTATGCTTCAAGTCGTACGATAGCACAGAATCGTAGTATCGAGATGCTGATGTCTGAAATCGATGCATGCTGACTACGTAGGCTGATCGAGATCGAT SEQ ID NO:204

Primer sequences    PRIMER A = ACGAAGTTCAGCATC  SEQ ID NO:205   PRIMER B = TAAGCTAGGGCCAGT  SEQ ID NO:209
(all 5'->3')        PRIMER C = GTAGCTGATTCGATT  SEQ ID NO:206   PRIMER D = ATGATCCATGTTACT  SEQ ID NO:210
                    PRIMER E = ATTCTGGTATGCTAG  SEQ ID NO:207   PRIMER F = GATCTTTAGCTAGTC  SEQ ID NO:211
                    PRIMER G = ATAATCCGTAGCTAT  SEQ ID NO:208   PRIMER H = AGTCGTACGTAGCTA  SEQ ID NO:212

SEQUENCE X RESULTS:

<< solid-support-bound primers >>

| | A₁ | B₁ | C₁ | D₁ | E₁ | F₁ | G₁ | H₁ |
|---|---|---|---|---|---|---|---|---|
| A₂ | - | - | - | - | - | - | - | - |
| B₂ | - | - | + | - | - | - | - | - |
| C₂ | - | + | - | - | - | - | - | - |
| D₂ | - | - | - | - | - | - | - | - |
| E₂ | - | - | - | - | - | - | - | - |
| F₂ | - | - | - | - | - | - | - | - |
| G₂ | - | - | - | - | - | - | - | - |
| H₂ | - | - | - | - | - | - | - | - | primers for labelled strand

SEQUENCE Y RESULTS:

| | A₁ | B₁ | C₁ | D₁ | E₁ | F₁ | G₁ | H₁ |
|---|---|---|---|---|---|---|---|---|
| A₂ | - | - | - | - | - | - | - | + |
| B₂ | - | - | - | - | - | - | - | - |
| C₂ | - | - | - | - | - | - | - | - |
| D₂ | - | - | - | - | - | - | - | - |
| E₂ | - | - | - | - | - | - | - | - |
| F₂ | - | - | - | - | - | - | - | - |
| G₂ | - | - | - | - | - | - | - | - |
| H₂ | + | - | - | - | - | - | - | - | primers for labelled strand

Figure 18

SEQUENCE LISTING

```
<160> NUMBER OF SEQ ID NOS: 212

<210> SEQ ID NO 1
<211> LENGTH: 10
<212> TYPE: DNA
<213> ORGANISM: Artificial Sequence
<220> FEATURE:
<223> OTHER INFORMATION: chemically synthesized

<400> SEQUENCE: 1
gtttcgctcc                                                          10

<210> SEQ ID NO 2
<211> LENGTH: 10
<212> TYPE: DNA
<213> ORGANISM: Artificial Sequence
<220> FEATURE:
<223> OTHER INFORMATION: chemically synthesized

<400> SEQUENCE: 2
tgatccctgg                                                          10

<210> SEQ ID NO 3
<211> LENGTH: 10
<212> TYPE: DNA
<213> ORGANISM: Artificial Sequence
<220> FEATURE:
<223> OTHER INFORMATION: chemically synthesized

<400> SEQUENCE: 3
catcccctg                                                           10

<210> SEQ ID NO 4
<211> LENGTH: 10
<212> TYPE: DNA
<213> ORGANISM: Artificial Sequence
<220> FEATURE:
<223> OTHER INFORMATION: chemically synthesized

<400> SEQUENCE: 4
ggactggagt                                                          10

<210> SEQ ID NO 5
<211> LENGTH: 10
<212> TYPE: DNA
<213> ORGANISM: Artificial Sequence
<220> FEATURE:
<223> OTHER INFORMATION: chemically synthesized

<400> SEQUENCE: 5
```

-continued tgcgcccttc                                                                   10

<210> SEQ ID NO 6
<211> LENGTH: 10
<212> TYPE: DNA
<213> ORGANISM: Artificial Sequence
<220> FEATURE:
<223> OTHER INFORMATION: chemically synthesized

<400> SEQUENCE: 6
cccaaggtcc                                                                   10

<210> SEQ ID NO 7
<211> LENGTH: 10
<212> TYPE: DNA
<213> ORGANISM: Artificial Sequence
<220> FEATURE:
<223> OTHER INFORMATION: chemically synthesized

<400> SEQUENCE: 7
ggtgcgggaa                                                                   10

<210> SEQ ID NO 8
<211> LENGTH: 10
<212> TYPE: DNA
<213> ORGANISM: Artificial Sequence
<220> FEATURE:
<223> OTHER INFORMATION: chemically synthesized

<400> SEQUENCE: 8
ccagatgcac                                                                   10

<210> SEQ ID NO 9
<211> LENGTH: 10
<212> TYPE: DNA
<213> ORGANISM: Artificial Sequence
<220> FEATURE:
<223> OTHER INFORMATION: chemically synthesized

<400> SEQUENCE: 9
gtgacatgcc                                                                   10

<210> SEQ ID NO 10
<211> LENGTH: 10
<212> TYPE: DNA
<213> ORGANISM: Artificial Sequence
<220> FEATURE:
<223> OTHER INFORMATION: chemically synthesized

<400> SEQUENCE: 10
tcagggaggt                                                                   10

<210> SEQ ID NO 11
<211> LENGTH: 10
<212> TYPE: DNA
<213> ORGANISM: Artificial Sequence
<220> FEATURE:
<223> OTHER INFORMATION: chemically synthesized

<400> SEQUENCE: 11
cccggcataa                                                                   10

<210> SEQ ID NO 12
<211> LENGTH: 10
<212> TYPE: DNA
<213> ORGANISM: Artificial Sequence

```
<220> FEATURE:
<223> OTHER INFORMATION: chemically synthesized

<400> SEQUENCE: 12
cccgttggga                                                              10

<210> SEQ ID NO 13
<211> LENGTH: 10
<212> TYPE: DNA
<213> ORGANISM: Artificial Sequence
<220> FEATURE:
<223> OTHER INFORMATION: chemically synthesized

<400> SEQUENCE: 13
tctccgcttg                                                              10

<210> SEQ ID NO 14
<211> LENGTH: 10
<212> TYPE: DNA
<213> ORGANISM: Artificial Sequence
<220> FEATURE:
<223> OTHER INFORMATION: chemically synthesized

<400> SEQUENCE: 14
ccgaacacgg                                                              10

<210> SEQ ID NO 15
<211> LENGTH: 10
<212> TYPE: DNA
<213> ORGANISM: Artificial Sequence
<220> FEATURE:
<223> OTHER INFORMATION: chemically synthesized

<400> SEQUENCE: 15
ctccatgggg                                                              10

<210> SEQ ID NO 16
<211> LENGTH: 10
<212> TYPE: DNA
<213> ORGANISM: Artificial Sequence
<220> FEATURE:
<223> OTHER INFORMATION: chemically synthesized

<400> SEQUENCE: 16
ggcacgtaag                                                              10

<210> SEQ ID NO 17
<211> LENGTH: 10
<212> TYPE: DNA
<213> ORGANISM: Artificial Sequence
<220> FEATURE:
<223> OTHER INFORMATION: chemically synthesized

<400> SEQUENCE: 17
acgtagcgtc                                                              10

<210> SEQ ID NO 18
<211> LENGTH: 10
<212> TYPE: DNA
<213> ORGANISM: Artificial Sequence
<220> FEATURE:
<223> OTHER INFORMATION: chemically synthesized

<400> SEQUENCE: 18
ctgttgctac                                                              10
```

-continued

<210> SEQ ID NO 19
<211> LENGTH: 10
<212> TYPE: DNA
<213> ORGANISM: Artificial Sequence
<220> FEATURE:
<223> OTHER INFORMATION: chemically synthesized

<400> SEQUENCE: 19
aagtccgctc                                                            10

<210> SEQ ID NO 20
<211> LENGTH: 10
<212> TYPE: DNA
<213> ORGANISM: Artificial Sequence
<220> FEATURE:
<223> OTHER INFORMATION: chemically synthesized

<400> SEQUENCE: 20
cccagtcact                                                            10

<210> SEQ ID NO 21
<211> LENGTH: 10
<212> TYPE: DNA
<213> ORGANISM: Artificial Sequence
<220> FEATURE:
<223> OTHER INFORMATION: chemically synthesized

<400> SEQUENCE: 21
gggccactca                                                            10

<210> SEQ ID NO 22
<211> LENGTH: 10
<212> TYPE: DNA
<213> ORGANISM: Artificial Sequence
<220> FEATURE:
<223> OTHER INFORMATION: chemically synthesized

<400> SEQUENCE: 22
ggagagactc                                                            10

<210> SEQ ID NO 23
<211> LENGTH: 10
<212> TYPE: DNA
<213> ORGANISM: Artificial Sequence
<220> FEATURE:
<223> OTHER INFORMATION: chemically synthesized

<400> SEQUENCE: 23
tccactcctg                                                            10

<210> SEQ ID NO 24
<211> LENGTH: 10
<212> TYPE: DNA
<213> ORGANISM: Artificial Sequence
<220> FEATURE:
<223> OTHER INFORMATION: chemically synthesized

<400> SEQUENCE: 24
cacagaggga                                                            10

<210> SEQ ID NO 25
<211> LENGTH: 10
<212> TYPE: DNA
<213> ORGANISM: Artificial Sequence
<220> FEATURE:
<223> OTHER INFORMATION: chemically synthesized

```
<400> SEQUENCE: 25
gggtttggca                                                              10

<210> SEQ ID NO 26
<211> LENGTH: 10
<212> TYPE: DNA
<213> ORGANISM: Artificial Sequence
<220> FEATURE:
<223> OTHER INFORMATION: chemically synthesized

<400> SEQUENCE: 26
gtggcatctc                                                              10

<210> SEQ ID NO 27
<211> LENGTH: 10
<212> TYPE: DNA
<213> ORGANISM: Artificial Sequence
<220> FEATURE:
<223> OTHER INFORMATION: chemically synthesized

<400> SEQUENCE: 27
catcgccgca                                                              10

<210> SEQ ID NO 28
<211> LENGTH: 10
<212> TYPE: DNA
<213> ORGANISM: Artificial Sequence
<220> FEATURE:
<223> OTHER INFORMATION: chemically synthesized

<400> SEQUENCE: 28
acagcctgct                                                              10

<210> SEQ ID NO 29
<211> LENGTH: 10
<212> TYPE: DNA
<213> ORGANISM: Artificial Sequence
<220> FEATURE:
<223> OTHER INFORMATION: chemically synthesized

<400> SEQUENCE: 29
ggctgcaatc                                                              10

<210> SEQ ID NO 30
<211> LENGTH: 10
<212> TYPE: DNA
<213> ORGANISM: Artificial Sequence
<220> FEATURE:
<223> OTHER INFORMATION: chemically synthesized

<400> SEQUENCE: 30
ggctgcgaca                                                              10

<210> SEQ ID NO 31
<211> LENGTH: 10
<212> TYPE: DNA
<213> ORGANISM: Artificial Sequence
<220> FEATURE:
<223> OTHER INFORMATION: chemically synthesized

<400> SEQUENCE: 31
caaagggcgg                                                              10

<210> SEQ ID NO 32
```

```
<210> SEQ ID NO 32
<211> LENGTH: 10
<212> TYPE: DNA
<213> ORGANISM: Artificial Sequence
<220> FEATURE:
<223> OTHER INFORMATION: chemically synthesized

<400> SEQUENCE: 32
ctgaaccgct                                                           10

<210> SEQ ID NO 33
<211> LENGTH: 10
<212> TYPE: DNA
<213> ORGANISM: Artificial Sequence
<220> FEATURE:
<223> OTHER INFORMATION: chemically synthesized

<400> SEQUENCE: 33
tctcgcctac                                                           10

<210> SEQ ID NO 34
<211> LENGTH: 10
<212> TYPE: DNA
<213> ORGANISM: Artificial Sequence
<220> FEATURE:
<223> OTHER INFORMATION: chemically synthesized

<400> SEQUENCE: 34
gtaggcctca                                                           10

<210> SEQ ID NO 35
<211> LENGTH: 10
<212> TYPE: DNA
<213> ORGANISM: Artificial Sequence
<220> FEATURE:
<223> OTHER INFORMATION: chemically synthesized

<400> SEQUENCE: 35
accgcatggg                                                           10

<210> SEQ ID NO 36
<211> LENGTH: 10
<212> TYPE: DNA
<213> ORGANISM: Artificial Sequence
<220> FEATURE:
<223> OTHER INFORMATION: chemically synthesized

<400> SEQUENCE: 36
ggcatcggct                                                           10

<210> SEQ ID NO 37
<211> LENGTH: 10
<212> TYPE: DNA
<213> ORGANISM: Artificial Sequence
<220> FEATURE:
<223> OTHER INFORMATION: chemically synthesized

<400> SEQUENCE: 37
agccgttcag                                                           10

<210> SEQ ID NO 38
<211> LENGTH: 10
<212> TYPE: DNA
<213> ORGANISM: Artificial Sequence
<220> FEATURE:
<223> OTHER INFORMATION: chemically synthesized

<400> SEQUENCE: 38
```

```
gggtccaaag                                                                      10

<210> SEQ ID NO 39
<211> LENGTH: 10
<212> TYPE: DNA
<213> ORGANISM: Artificial Sequence
<220> FEATURE:
<223> OTHER INFORMATION: chemically synthesized

<400> SEQUENCE: 39
ctatcctgcc                                                                      10

<210> SEQ ID NO 40
<211> LENGTH: 10
<212> TYPE: DNA
<213> ORGANISM: Artificial Sequence
<220> FEATURE:
<223> OTHER INFORMATION: chemically synthesized

<400> SEQUENCE: 40
gtcgtagcgg                                                                      10

<210> SEQ ID NO 41
<211> LENGTH: 10
<212> TYPE: DNA
<213> ORGANISM: Artificial Sequence
<220> FEATURE:
<223> OTHER INFORMATION: chemically synthesized

<400> SEQUENCE: 41
actccacgtc                                                                      10

<210> SEQ ID NO 42
<211> LENGTH: 10
<212> TYPE: DNA
<213> ORGANISM: Artificial Sequence
<220> FEATURE:
<223> OTHER INFORMATION: chemically synthesized

<400> SEQUENCE: 42
caccgcagtt                                                                      10

<210> SEQ ID NO 43
<211> LENGTH: 10
<212> TYPE: DNA
<213> ORGANISM: Artificial Sequence
<220> FEATURE:
<223> OTHER INFORMATION: chemically synthesized

<400> SEQUENCE: 43
agccaggctg                                                                      10

<210> SEQ ID NO 44
<211> LENGTH: 10
<212> TYPE: DNA
<213> ORGANISM: Artificial Sequence
<220> FEATURE:
<223> OTHER INFORMATION: chemically synthesized

<400> SEQUENCE: 44
ggcgtaagtc                                                                      10

<210> SEQ ID NO 45
<211> LENGTH: 10
<212> TYPE: DNA
```

<213> ORGANISM: Artificial Sequence
<220> FEATURE:
<223> OTHER INFORMATION: chemically synthesized

<400> SEQUENCE: 45
gggtgcagtt                                                          10

<210> SEQ ID NO 46
<211> LENGTH: 10
<212> TYPE: DNA
<213> ORGANISM: Artificial Sequence
<220> FEATURE:
<223> OTHER INFORMATION: chemically synthesized

<400> SEQUENCE: 46
cacaccgtgt                                                          10

<210> SEQ ID NO 47
<211> LENGTH: 10
<212> TYPE: DNA
<213> ORGANISM: Artificial Sequence
<220> FEATURE:
<223> OTHER INFORMATION: chemically synthesized

<400> SEQUENCE: 47
gtcctcgtgt                                                          10

<210> SEQ ID NO 48
<211> LENGTH: 10
<212> TYPE: DNA
<213> ORGANISM: Artificial Sequence
<220> FEATURE:
<223> OTHER INFORMATION: chemically synthesized

<400> SEQUENCE: 48
acggttccac                                                          10

<210> SEQ ID NO 49
<211> LENGTH: 10
<212> TYPE: DNA
<213> ORGANISM: Artificial Sequence
<220> FEATURE:
<223> OTHER INFORMATION: chemically synthesized

<400> SEQUENCE: 49
gtcttgggca                                                          10

<210> SEQ ID NO 50
<211> LENGTH: 10
<212> TYPE: DNA
<213> ORGANISM: Artificial Sequence
<220> FEATURE:
<223> OTHER INFORMATION: chemically synthesized

<400> SEQUENCE: 50
gtcacctgct                                                          10

<210> SEQ ID NO 51
<211> LENGTH: 10
<212> TYPE: DNA
<213> ORGANISM: Artificial Sequence
<220> FEATURE:
<223> OTHER INFORMATION: chemically synthesized

<400> SEQUENCE: 51
tgctctgccc                                                          10

<210> SEQ ID NO 52
<211> LENGTH: 10
<212> TYPE: DNA
<213> ORGANISM: Artificial Sequence
<220> FEATURE:
<223> OTHER INFORMATION: chemically synthesized

<400> SEQUENCE: 52
ggtgacgcag                                                          10

<210> SEQ ID NO 53
<211> LENGTH: 10
<212> TYPE: DNA
<213> ORGANISM: Artificial Sequence
<220> FEATURE:
<223> OTHER INFORMATION: chemically synthesized

<400> SEQUENCE: 53
gtccacacgg                                                          10

<210> SEQ ID NO 54
<211> LENGTH: 10
<212> TYPE: DNA
<213> ORGANISM: Artificial Sequence
<220> FEATURE:
<223> OTHER INFORMATION: chemically synthesized

<400> SEQUENCE: 54
tggggactc                                                           10

<210> SEQ ID NO 55
<211> LENGTH: 10
<212> TYPE: DNA
<213> ORGANISM: Artificial Sequence
<220> FEATURE:
<223> OTHER INFORMATION: chemically synthesized

<400> SEQUENCE: 55
ctgctgggac                                                          10

<210> SEQ ID NO 56
<211> LENGTH: 10
<212> TYPE: DNA
<213> ORGANISM: Artificial Sequence
<220> FEATURE:
<223> OTHER INFORMATION: chemically synthesized

<400> SEQUENCE: 56
aagacccctc                                                          10

<210> SEQ ID NO 57
<211> LENGTH: 10
<212> TYPE: DNA
<213> ORGANISM: Artificial Sequence
<220> FEATURE:
<223> OTHER INFORMATION: chemically synthesized

<400> SEQUENCE: 57
agatgcagcc                                                          10

<210> SEQ ID NO 58
<211> LENGTH: 10
<212> TYPE: DNA
<213> ORGANISM: Artificial Sequence
<220> FEATURE:

```
<223> OTHER INFORMATION: chemically synthesized

<400> SEQUENCE: 58
tcaccacggt                                                              10

<210> SEQ ID NO 59
<211> LENGTH: 10
<212> TYPE: DNA
<213> ORGANISM: Artificial Sequence
<220> FEATURE:
<223> OTHER INFORMATION: chemically synthesized

<400> SEQUENCE: 59
cttcacccga                                                              10

<210> SEQ ID NO 60
<211> LENGTH: 10
<212> TYPE: DNA
<213> ORGANISM: Artificial Sequence
<220> FEATURE:
<223> OTHER INFORMATION: chemically synthesized

<400> SEQUENCE: 60
caccaggtga                                                              10

<210> SEQ ID NO 61
<211> LENGTH: 10
<212> TYPE: DNA
<213> ORGANISM: Artificial Sequence
<220> FEATURE:
<223> OTHER INFORMATION: chemically synthesized

<400> SEQUENCE: 61
tcgttccgca                                                              10

<210> SEQ ID NO 62
<211> LENGTH: 10
<212> TYPE: DNA
<213> ORGANISM: Artificial Sequence
<220> FEATURE:
<223> OTHER INFORMATION: chemically synthesized

<400> SEQUENCE: 62
cctctcgaca                                                              10

<210> SEQ ID NO 63
<211> LENGTH: 10
<212> TYPE: DNA
<213> ORGANISM: Artificial Sequence
<220> FEATURE:
<223> OTHER INFORMATION: chemically synthesized

<400> SEQUENCE: 63
cataccgtgg                                                              10

<210> SEQ ID NO 64
<211> LENGTH: 10
<212> TYPE: DNA
<213> ORGANISM: Artificial Sequence
<220> FEATURE:
<223> OTHER INFORMATION: chemically synthesized

<400> SEQUENCE: 64
tgagcctcac                                                              10
```

```
<210> SEQ ID NO 65
<211> LENGTH: 10
<212> TYPE: DNA
<213> ORGANISM: Artificial Sequence
<220> FEATURE:
<223> OTHER INFORMATION: chemically synthesized

<400> SEQUENCE: 65
aagcccgagg                                                          10

<210> SEQ ID NO 66
<211> LENGTH: 10
<212> TYPE: DNA
<213> ORGANISM: Artificial Sequence
<220> FEATURE:
<223> OTHER INFORMATION: chemically synthesized

<400> SEQUENCE: 66
ccacgggaag                                                          10

<210> SEQ ID NO 67
<211> LENGTH: 10
<212> TYPE: DNA
<213> ORGANISM: Artificial Sequence
<220> FEATURE:
<223> OTHER INFORMATION: chemically synthesized

<400> SEQUENCE: 67
cagcactgac                                                          10

<210> SEQ ID NO 68
<211> LENGTH: 10
<212> TYPE: DNA
<213> ORGANISM: Artificial Sequence
<220> FEATURE:
<223> OTHER INFORMATION: chemically synthesized

<400> SEQUENCE: 68
cctccagtgt                                                          10

<210> SEQ ID NO 69
<211> LENGTH: 10
<212> TYPE: DNA
<213> ORGANISM: Artificial Sequence
<220> FEATURE:
<223> OTHER INFORMATION: chemically synthesized

<400> SEQUENCE: 69
tcccacgcaa                                                          10

<210> SEQ ID NO 70
<211> LENGTH: 10
<212> TYPE: DNA
<213> ORGANISM: Artificial Sequence
<220> FEATURE:
<223> OTHER INFORMATION: chemically synthesized

<400> SEQUENCE: 70
tcagagcgcc                                                          10

<210> SEQ ID NO 71
<211> LENGTH: 10
<212> TYPE: DNA
<213> ORGANISM: Artificial Sequence
<220> FEATURE:
<223> OTHER INFORMATION: chemically synthesized
```

```
<400> SEQUENCE: 71
caagggcaga                                                              10

<210> SEQ ID NO 72
<211> LENGTH: 10
<212> TYPE: DNA
<213> ORGANISM: Artificial Sequence
<220> FEATURE:
<223> OTHER INFORMATION: chemically synthesized

<400> SEQUENCE: 72
ggcaggctgt                                                              10

<210> SEQ ID NO 73
<211> LENGTH: 10
<212> TYPE: DNA
<213> ORGANISM: Artificial Sequence
<220> FEATURE:
<223> OTHER INFORMATION: chemically synthesized

<400> SEQUENCE: 73
aacggcgaca                                                              10

<210> SEQ ID NO 74
<211> LENGTH: 10
<212> TYPE: DNA
<213> ORGANISM: Artificial Sequence
<220> FEATURE:
<223> OTHER INFORMATION: chemically synthesized

<400> SEQUENCE: 74
cacccctgag                                                              10

<210> SEQ ID NO 75
<211> LENGTH: 10
<212> TYPE: DNA
<213> ORGANISM: Artificial Sequence
<220> FEATURE:
<223> OTHER INFORMATION: chemically synthesized

<400> SEQUENCE: 75
ccttcggaag                                                              10

<210> SEQ ID NO 76
<211> LENGTH: 10
<212> TYPE: DNA
<213> ORGANISM: Artificial Sequence
<220> FEATURE:
<223> OTHER INFORMATION: chemically synthesized

<400> SEQUENCE: 76
aaggctcacc                                                              10

<210> SEQ ID NO 77
<211> LENGTH: 10
<212> TYPE: DNA
<213> ORGANISM: Artificial Sequence
<220> FEATURE:
<223> OTHER INFORMATION: chemically synthesized

<400> SEQUENCE: 77
agagccgtca                                                              10

<210> SEQ ID NO 78
<211> LENGTH: 10
```

```
<212> TYPE: DNA
<213> ORGANISM: Artificial Sequence
<220> FEATURE:
<223> OTHER INFORMATION: chemically synthesized

<400> SEQUENCE: 78
aggcagagca                                                          10

<210> SEQ ID NO 79
<211> LENGTH: 10
<212> TYPE: DNA
<213> ORGANISM: Artificial Sequence
<220> FEATURE:
<223> OTHER INFORMATION: chemically synthesized

<400> SEQUENCE: 79
agcagcgcac                                                          10

<210> SEQ ID NO 80
<211> LENGTH: 10
<212> TYPE: DNA
<213> ORGANISM: Artificial Sequence
<220> FEATURE:
<223> OTHER INFORMATION: chemically synthesized

<400> SEQUENCE: 80
caaacgtggg                                                          10

<210> SEQ ID NO 81
<211> LENGTH: 10
<212> TYPE: DNA
<213> ORGANISM: Artificial Sequence
<220> FEATURE:
<223> OTHER INFORMATION: chemically synthesized

<400> SEQUENCE: 81
aagtgcacgg                                                          10

<210> SEQ ID NO 82
<211> LENGTH: 10
<212> TYPE: DNA
<213> ORGANISM: Artificial Sequence
<220> FEATURE:
<223> OTHER INFORMATION: chemically synthesized

<400> SEQUENCE: 82
ccctactggt                                                          10

<210> SEQ ID NO 83
<211> LENGTH: 10
<212> TYPE: DNA
<213> ORGANISM: Artificial Sequence
<220> FEATURE:
<223> OTHER INFORMATION: chemically synthesized

<400> SEQUENCE: 83
ggcaggcaag                                                          10

<210> SEQ ID NO 84
<211> LENGTH: 10
<212> TYPE: DNA
<213> ORGANISM: Artificial Sequence
<220> FEATURE:
<223> OTHER INFORMATION: chemically synthesized

<400> SEQUENCE: 84
```
tcgcttctcc 10

<210> SEQ ID NO 85
<211> LENGTH: 10
<212> TYPE: DNA
<213> ORGANISM: Artificial Sequence
<220> FEATURE:
<223> OTHER INFORMATION: chemically synthesized

<400> SEQUENCE: 85
aagaggccag 10

<210> SEQ ID NO 86
<211> LENGTH: 10
<212> TYPE: DNA
<213> ORGANISM: Artificial Sequence
<220> FEATURE:
<223> OTHER INFORMATION: chemically synthesized

<400> SEQUENCE: 86
tgccgcactt 10

<210> SEQ ID NO 87
<211> LENGTH: 10
<212> TYPE: DNA
<213> ORGANISM: Artificial Sequence
<220> FEATURE:
<223> OTHER INFORMATION: chemically synthesized

<400> SEQUENCE: 87
acgagcatgg 10

<210> SEQ ID NO 88
<211> LENGTH: 10
<212> TYPE: DNA
<213> ORGANISM: Artificial Sequence
<220> FEATURE:
<223> OTHER INFORMATION: chemically synthesized

<400> SEQUENCE: 88
aagcccccca 10

<210> SEQ ID NO 89
<211> LENGTH: 10
<212> TYPE: DNA
<213> ORGANISM: Artificial Sequence
<220> FEATURE:
<223> OTHER INFORMATION: chemically synthesized

<400> SEQUENCE: 89
tcgctggtgt 10

<210> SEQ ID NO 90
<211> LENGTH: 10
<212> TYPE: DNA
<213> ORGANISM: Artificial Sequence
<220> FEATURE:
<223> OTHER INFORMATION: chemically synthesized

<400> SEQUENCE: 90
tcgggcatca 10

<210> SEQ ID NO 91
<211> LENGTH: 10
<212> TYPE: DNA
<213> ORGANISM: Artificial Sequence

```
<220> FEATURE:
<223> OTHER INFORMATION: chemically synthesized

<400> SEQUENCE: 91
gggaacccgt                                                                    10

<210> SEQ ID NO 92
<211> LENGTH: 10
<212> TYPE: DNA
<213> ORGANISM: Artificial Sequence
<220> FEATURE:
<223> OTHER INFORMATION: chemically synthesized

<400> SEQUENCE: 92
tcgctgcgga                                                                    10

<210> SEQ ID NO 93
<211> LENGTH: 10
<212> TYPE: DNA
<213> ORGANISM: Artificial Sequence
<220> FEATURE:
<223> OTHER INFORMATION: chemically synthesized

<400> SEQUENCE: 93
aaggctgctg                                                                    10

<210> SEQ ID NO 94
<211> LENGTH: 10
<212> TYPE: DNA
<213> ORGANISM: Artificial Sequence
<220> FEATURE:
<223> OTHER INFORMATION: chemically synthesized

<400> SEQUENCE: 94
gggggagatg                                                                    10

<210> SEQ ID NO 95
<211> LENGTH: 10
<212> TYPE: DNA
<213> ORGANISM: Artificial Sequence
<220> FEATURE:
<223> OTHER INFORMATION: chemically synthesized

<400> SEQUENCE: 95
ctgtgtgctc                                                                    10

<210> SEQ ID NO 96
<211> LENGTH: 10
<212> TYPE: DNA
<213> ORGANISM: Artificial Sequence
<220> FEATURE:
<223> OTHER INFORMATION: chemically synthesized

<400> SEQUENCE: 96
ggcgcgttag                                                                    10

<210> SEQ ID NO 97
<211> LENGTH: 10
<212> TYPE: DNA
<213> ORGANISM: Artificial Sequence
<220> FEATURE:
<223> OTHER INFORMATION: chemically synthesized

<400> SEQUENCE: 97
gacgagcagg                                                                    10
```

```
<210> SEQ ID NO 98
<211> LENGTH: 10
<212> TYPE: DNA
<213> ORGANISM: Artificial Sequence
<220> FEATURE:
<223> OTHER INFORMATION: chemically synthesized

<400> SEQUENCE: 98
ggctgccagt                                                              10

<210> SEQ ID NO 99
<211> LENGTH: 10
<212> TYPE: DNA
<213> ORGANISM: Artificial Sequence
<220> FEATURE:
<223> OTHER INFORMATION: chemically synthesized

<400> SEQUENCE: 99
tggagtcccc                                                              10

<210> SEQ ID NO 100
<211> LENGTH: 10
<212> TYPE: DNA
<213> ORGANISM: Artificial Sequence
<220> FEATURE:
<223> OTHER INFORMATION: chemically synthesized

<400> SEQUENCE: 100
cccgtctacc                                                              10

<210> SEQ ID NO 101
<211> LENGTH: 10
<212> TYPE: DNA
<213> ORGANISM: Artificial Sequence
<220> FEATURE:
<223> OTHER INFORMATION: chemically synthesized

<400> SEQUENCE: 101
gtagacccgt                                                              10

<210> SEQ ID NO 102
<211> LENGTH: 10
<212> TYPE: DNA
<213> ORGANISM: Artificial Sequence
<220> FEATURE:
<223> OTHER INFORMATION: chemically synthesized

<400> SEQUENCE: 102
ccttgacgca                                                              10

<210> SEQ ID NO 103
<211> LENGTH: 10
<212> TYPE: DNA
<213> ORGANISM: Artificial Sequence
<220> FEATURE:
<223> OTHER INFORMATION: chemically synthesized

<400> SEQUENCE: 103
ttcccccgct                                                              10

<210> SEQ ID NO 104
<211> LENGTH: 10
<212> TYPE: DNA
<213> ORGANISM: Artificial Sequence
<220> FEATURE:
<223> OTHER INFORMATION: chemically synthesized
```

-continued

<400> SEQUENCE: 104
tccgctctgg                                                           10

<210> SEQ ID NO 105
<211> LENGTH: 10
<212> TYPE: DNA
<213> ORGANISM: Artificial Sequence
<220> FEATURE:
<223> OTHER INFORMATION: chemically synthesized

<400> SEQUENCE: 105
ggagggtgtt                                                           10

<210> SEQ ID NO 106
<211> LENGTH: 10
<212> TYPE: DNA
<213> ORGANISM: Artificial Sequence
<220> FEATURE:
<223> OTHER INFORMATION: chemically synthesized

<400> SEQUENCE: 106
gagtctcagg                                                           10

<210> SEQ ID NO 107
<211> LENGTH: 10
<212> TYPE: DNA
<213> ORGANISM: Artificial Sequence
<220> FEATURE:
<223> OTHER INFORMATION: chemically synthesized

<400> SEQUENCE: 107
ttatcgcccc                                                           10

<210> SEQ ID NO 108
<211> LENGTH: 10
<212> TYPE: DNA
<213> ORGANISM: Artificial Sequence
<220> FEATURE:
<223> OTHER INFORMATION: chemically synthesized

<400> SEQUENCE: 108
cccgattcgg                                                           10

<210> SEQ ID NO 109
<211> LENGTH: 10
<212> TYPE: DNA
<213> ORGANISM: Artificial Sequence
<220> FEATURE:
<223> OTHER INFORMATION: chemically synthesized

<400> SEQUENCE: 109
tgcggctgag                                                           10

<210> SEQ ID NO 110
<211> LENGTH: 10
<212> TYPE: DNA
<213> ORGANISM: Artificial Sequence
<220> FEATURE:
<223> OTHER INFORMATION: chemically synthesized

<400> SEQUENCE: 110
acgcacaacc                                                           10

<210> SEQ ID NO 111

```
<211> LENGTH: 10
<212> TYPE: DNA
<213> ORGANISM: Artificial Sequence
<220> FEATURE:
<223> OTHER INFORMATION: chemically synthesized

<400> SEQUENCE: 111
actcctgcga                                                            10

<210> SEQ ID NO 112
<211> LENGTH: 10
<212> TYPE: DNA
<213> ORGANISM: Artificial Sequence
<220> FEATURE:
<223> OTHER INFORMATION: chemically synthesized

<400> SEQUENCE: 112
gtcccgtggt                                                            10

<210> SEQ ID NO 113
<211> LENGTH: 10
<212> TYPE: DNA
<213> ORGANISM: Artificial Sequence
<220> FEATURE:
<223> OTHER INFORMATION: chemically synthesized

<400> SEQUENCE: 113
ccacactacc                                                            10

<210> SEQ ID NO 114
<211> LENGTH: 10
<212> TYPE: DNA
<213> ORGANISM: Artificial Sequence
<220> FEATURE:
<223> OTHER INFORMATION: chemically synthesized

<400> SEQUENCE: 114
cacccggatc                                                            10

<210> SEQ ID NO 115
<211> LENGTH: 10
<212> TYPE: DNA
<213> ORGANISM: Artificial Sequence
<220> FEATURE:
<223> OTHER INFORMATION: chemically synthesized

<400> SEQUENCE: 115
tgtagcaggg                                                            10

<210> SEQ ID NO 116
<211> LENGTH: 10
<212> TYPE: DNA
<213> ORGANISM: Artificial Sequence
<220> FEATURE:
<223> OTHER INFORMATION: chemically synthesized

<400> SEQUENCE: 116
gacaggaggt                                                            10

<210> SEQ ID NO 117
<211> LENGTH: 10
<212> TYPE: DNA
<213> ORGANISM: Artificial Sequence
<220> FEATURE:
<223> OTHER INFORMATION: chemically synthesized

<400> SEQUENCE: 117
```

```
cagtgctgtg                                                          10

<210> SEQ ID NO 118
<211> LENGTH: 10
<212> TYPE: DNA
<213> ORGANISM: Artificial Sequence
<220> FEATURE:
<223> OTHER INFORMATION: chemically synthesized

<400> SEQUENCE: 118
gtcagagtcc                                                          10

<210> SEQ ID NO 119
<211> LENGTH: 10
<212> TYPE: DNA
<213> ORGANISM: Artificial Sequence
<220> FEATURE:
<223> OTHER INFORMATION: chemically synthesized

<400> SEQUENCE: 119
agcatggctc                                                          10

<210> SEQ ID NO 120
<211> LENGTH: 10
<212> TYPE: DNA
<213> ORGANISM: Artificial Sequence
<220> FEATURE:
<223> OTHER INFORMATION: chemically synthesized

<400> SEQUENCE: 120
tggcgtcctt                                                          10

<210> SEQ ID NO 121
<211> LENGTH: 10
<212> TYPE: DNA
<213> ORGANISM: Artificial Sequence
<220> FEATURE:
<223> OTHER INFORMATION: chemically synthesized

<400> SEQUENCE: 121
ttccccgcga                                                          10

<210> SEQ ID NO 122
<211> LENGTH: 10
<212> TYPE: DNA
<213> ORGANISM: Artificial Sequence
<220> FEATURE:
<223> OTHER INFORMATION: chemically synthesized

<400> SEQUENCE: 122
gggtgtgtag                                                          10

<210> SEQ ID NO 123
<211> LENGTH: 10
<212> TYPE: DNA
<213> ORGANISM: Artificial Sequence
<220> FEATURE:
<223> OTHER INFORMATION: chemically synthesized

<400> SEQUENCE: 123
aggatgccag                                                          10

<210> SEQ ID NO 124
<211> LENGTH: 10
<212> TYPE: DNA
```

```
<213> ORGANISM: Artificial Sequence
<220> FEATURE:
<223> OTHER INFORMATION: chemically synthesized

<400> SEQUENCE: 124
aatgccgcag                                                              10

<210> SEQ ID NO 125
<211> LENGTH: 10
<212> TYPE: DNA
<213> ORGANISM: Artificial Sequence
<220> FEATURE:
<223> OTHER INFORMATION: chemically synthesized

<400> SEQUENCE: 125
ggatgccact                                                              10

<210> SEQ ID NO 126
<211> LENGTH: 10
<212> TYPE: DNA
<213> ORGANISM: Artificial Sequence
<220> FEATURE:
<223> OTHER INFORMATION: chemically synthesized

<400> SEQUENCE: 126
agacgatggg                                                              10

<210> SEQ ID NO 127
<211> LENGTH: 10
<212> TYPE: DNA
<213> ORGANISM: Artificial Sequence
<220> FEATURE:
<223> OTHER INFORMATION: chemically synthesized

<400> SEQUENCE: 127
aagcctgcga                                                              10

<210> SEQ ID NO 128
<211> LENGTH: 10
<212> TYPE: DNA
<213> ORGANISM: Artificial Sequence
<220> FEATURE:
<223> OTHER INFORMATION: chemically synthesized

<400> SEQUENCE: 128
gggtctcggt                                                              10

<210> SEQ ID NO 129
<211> LENGTH: 10
<212> TYPE: DNA
<213> ORGANISM: Artificial Sequence
<220> FEATURE:
<223> OTHER INFORMATION: chemically synthesized

<400> SEQUENCE: 129
ggtcgatctg                                                              10

<210> SEQ ID NO 130
<211> LENGTH: 10
<212> TYPE: DNA
<213> ORGANISM: Artificial Sequence
<220> FEATURE:
<223> OTHER INFORMATION: chemically synthesized

<400> SEQUENCE: 130
agtcgccctt                                                              10
```

<210> SEQ ID NO 131
<211> LENGTH: 10
<212> TYPE: DNA
<213> ORGANISM: Artificial Sequence
<220> FEATURE:
<223> OTHER INFORMATION: chemically synthesized

<400> SEQUENCE: 131
caatcgggtc                                                          10

<210> SEQ ID NO 132
<211> LENGTH: 10
<212> TYPE: DNA
<213> ORGANISM: Artificial Sequence
<220> FEATURE:
<223> OTHER INFORMATION: chemically synthesized

<400> SEQUENCE: 132
aagagggcgt                                                          10

<210> SEQ ID NO 133
<211> LENGTH: 10
<212> TYPE: DNA
<213> ORGANISM: Artificial Sequence
<220> FEATURE:
<223> OTHER INFORMATION: chemically synthesized

<400> SEQUENCE: 133
ggttcctctg                                                          10

<210> SEQ ID NO 134
<211> LENGTH: 10
<212> TYPE: DNA
<213> ORGANISM: Artificial Sequence
<220> FEATURE:
<223> OTHER INFORMATION: chemically synthesized

<400> SEQUENCE: 134
gaacgagggt                                                          10

<210> SEQ ID NO 135
<211> LENGTH: 10
<212> TYPE: DNA
<213> ORGANISM: Artificial Sequence
<220> FEATURE:
<223> OTHER INFORMATION: chemically synthesized

<400> SEQUENCE: 135
tttgccccgt                                                          10

<210> SEQ ID NO 136
<211> LENGTH: 10
<212> TYPE: DNA
<213> ORGANISM: Artificial Sequence
<220> FEATURE:
<223> OTHER INFORMATION: chemically synthesized

<400> SEQUENCE: 136
acggcgatga                                                          10

<210> SEQ ID NO 137
<211> LENGTH: 10
<212> TYPE: DNA
<213> ORGANISM: Artificial Sequence
<220> FEATURE:

```
<223> OTHER INFORMATION: chemically synthesized

<400> SEQUENCE: 137
gactctaacc                                                              10

<210> SEQ ID NO 138
<211> LENGTH: 10
<212> TYPE: DNA
<213> ORGANISM: Artificial Sequence
<220> FEATURE:
<223> OTHER INFORMATION: chemically synthesized

<400> SEQUENCE: 138
acgctgcgac                                                              10

<210> SEQ ID NO 139
<211> LENGTH: 10
<212> TYPE: DNA
<213> ORGANISM: Artificial Sequence
<220> FEATURE:
<223> OTHER INFORMATION: chemically synthesized

<400> SEQUENCE: 139
tggtgcactc                                                              10

<210> SEQ ID NO 140
<211> LENGTH: 10
<212> TYPE: DNA
<213> ORGANISM: Artificial Sequence
<220> FEATURE:
<223> OTHER INFORMATION: chemically synthesized

<400> SEQUENCE: 140
gacacagccc                                                              10

<210> SEQ ID NO 141
<211> LENGTH: 10
<212> TYPE: DNA
<213> ORGANISM: Artificial Sequence
<220> FEATURE:
<223> OTHER INFORMATION: chemically synthesized

<400> SEQUENCE: 141
gtccatgcag                                                              10

<210> SEQ ID NO 142
<211> LENGTH: 10
<212> TYPE: DNA
<213> ORGANISM: Artificial Sequence
<220> FEATURE:
<223> OTHER INFORMATION: chemically synthesized

<400> SEQUENCE: 142
aacggcggtc                                                              10

<210> SEQ ID NO 143
<211> LENGTH: 10
<212> TYPE: DNA
<213> ORGANISM: Artificial Sequence
<220> FEATURE:
<223> OTHER INFORMATION: chemically synthesized

<400> SEQUENCE: 143
cttccaggac                                                              10
```

```
<210> SEQ ID NO 144
<211> LENGTH: 10
<212> TYPE: DNA
<213> ORGANISM: Artificial Sequence
<220> FEATURE:
<223> OTHER INFORMATION: chemically synthesized

<400> SEQUENCE: 144
agccgggtaa                                                                10

<210> SEQ ID NO 145
<211> LENGTH: 10
<212> TYPE: DNA
<213> ORGANISM: Artificial Sequence
<220> FEATURE:
<223> OTHER INFORMATION: chemically synthesized

<400> SEQUENCE: 145
tgatgccgct                                                                10

<210> SEQ ID NO 146
<211> LENGTH: 10
<212> TYPE: DNA
<213> ORGANISM: Artificial Sequence
<220> FEATURE:
<223> OTHER INFORMATION: chemically synthesized

<400> SEQUENCE: 146
accgtgccgt                                                                10

<210> SEQ ID NO 147
<211> LENGTH: 10
<212> TYPE: DNA
<213> ORGANISM: Artificial Sequence
<220> FEATURE:
<223> OTHER INFORMATION: chemically synthesized

<400> SEQUENCE: 147
tgaccaggca                                                                10

<210> SEQ ID NO 148
<211> LENGTH: 10
<212> TYPE: DNA
<213> ORGANISM: Artificial Sequence
<220> FEATURE:
<223> OTHER INFORMATION: chemically synthesized

<400> SEQUENCE: 148
cacggaccga                                                                10

<210> SEQ ID NO 149
<211> LENGTH: 10
<212> TYPE: DNA
<213> ORGANISM: Artificial Sequence
<220> FEATURE:
<223> OTHER INFORMATION: chemically synthesized

<400> SEQUENCE: 149
tcgcagcgtt                                                                10

<210> SEQ ID NO 150
<211> LENGTH: 10
<212> TYPE: DNA
<213> ORGANISM: Artificial Sequence
<220> FEATURE:
<223> OTHER INFORMATION: chemically synthesized
```

```
<400> SEQUENCE: 150
ctgcaatggg                                                          10

<210> SEQ ID NO 151
<211> LENGTH: 10
<212> TYPE: DNA
<213> ORGANISM: Artificial Sequence
<220> FEATURE:
<223> OTHER INFORMATION: chemically synthesized

<400> SEQUENCE: 151
tttgcccgga                                                          10

<210> SEQ ID NO 152
<211> LENGTH: 10
<212> TYPE: DNA
<213> ORGANISM: Artificial Sequence
<220> FEATURE:
<223> OTHER INFORMATION: chemically synthesized

<400> SEQUENCE: 152
agggaacgag                                                          10

<210> SEQ ID NO 153
<211> LENGTH: 10
<212> TYPE: DNA
<213> ORGANISM: Artificial Sequence
<220> FEATURE:
<223> OTHER INFORMATION: chemically synthesized

<400> SEQUENCE: 153
ccacagcagt                                                          10

<210> SEQ ID NO 154
<211> LENGTH: 10
<212> TYPE: DNA
<213> ORGANISM: Artificial Sequence
<220> FEATURE:
<223> OTHER INFORMATION: chemically synthesized

<400> SEQUENCE: 154
acccccgaag                                                          10

<210> SEQ ID NO 155
<211> LENGTH: 10
<212> TYPE: DNA
<213> ORGANISM: Artificial Sequence
<220> FEATURE:
<223> OTHER INFORMATION: chemically synthesized

<400> SEQUENCE: 155
ggacccttac                                                          10

<210> SEQ ID NO 156
<211> LENGTH: 10
<212> TYPE: DNA
<213> ORGANISM: Artificial Sequence
<220> FEATURE:
<223> OTHER INFORMATION: chemically synthesized

<400> SEQUENCE: 156
ggtgactgtg                                                          10

<210> SEQ ID NO 157
<211> LENGTH: 10
```

```
<212> TYPE: DNA
<213> ORGANISM: Artificial Sequence
<220> FEATURE:
<223> OTHER INFORMATION: chemically synthesized

<400> SEQUENCE: 157
ctactgccgt                                                          10

<210> SEQ ID NO 158
<211> LENGTH: 10
<212> TYPE: DNA
<213> ORGANISM: Artificial Sequence
<220> FEATURE:
<223> OTHER INFORMATION: chemically synthesized

<400> SEQUENCE: 158
ggactgcaga                                                          10

<210> SEQ ID NO 159
<211> LENGTH: 10
<212> TYPE: DNA
<213> ORGANISM: Artificial Sequence
<220> FEATURE:
<223> OTHER INFORMATION: chemically synthesized

<400> SEQUENCE: 159
acggcgtatg                                                          10

<210> SEQ ID NO 160
<211> LENGTH: 10
<212> TYPE: DNA
<213> ORGANISM: Artificial Sequence
<220> FEATURE:
<223> OTHER INFORMATION: chemically synthesized

<400> SEQUENCE: 160
aacggtgacc                                                          10

<210> SEQ ID NO 161
<211> LENGTH: 10
<212> TYPE: DNA
<213> ORGANISM: Artificial Sequence
<220> FEATURE:
<223> OTHER INFORMATION: chemically synthesized

<400> SEQUENCE: 161
ctgcttaggg                                                          10

<210> SEQ ID NO 162
<211> LENGTH: 10
<212> TYPE: DNA
<213> ORGANISM: Artificial Sequence
<220> FEATURE:
<223> OTHER INFORMATION: chemically synthesized

<400> SEQUENCE: 162
acgccagttc                                                          10

<210> SEQ ID NO 163
<211> LENGTH: 10
<212> TYPE: DNA
<213> ORGANISM: Artificial Sequence
<220> FEATURE:
<223> OTHER INFORMATION: chemically synthesized

<400> SEQUENCE: 163
```

```
tggtcgcaga                                                          10

<210> SEQ ID NO 164
<211> LENGTH: 10
<212> TYPE: DNA
<213> ORGANISM: Artificial Sequence
<220> FEATURE:
<223> OTHER INFORMATION: chemically synthesized

<400> SEQUENCE: 164
ggacaccact                                                          10

<210> SEQ ID NO 165
<211> LENGTH: 10
<212> TYPE: DNA
<213> ORGANISM: Artificial Sequence
<220> FEATURE:
<223> OTHER INFORMATION: chemically synthesized

<400> SEQUENCE: 165
aagcggcctc                                                          10

<210> SEQ ID NO 166
<211> LENGTH: 10
<212> TYPE: DNA
<213> ORGANISM: Artificial Sequence
<220> FEATURE:
<223> OTHER INFORMATION: chemically synthesized

<400> SEQUENCE: 166
tcggcggttc                                                          10

<210> SEQ ID NO 167
<211> LENGTH: 10
<212> TYPE: DNA
<213> ORGANISM: Artificial Sequence
<220> FEATURE:
<223> OTHER INFORMATION: chemically synthesized

<400> SEQUENCE: 167
ggcttatgcc                                                          10

<210> SEQ ID NO 168
<211> LENGTH: 10
<212> TYPE: DNA
<213> ORGANISM: Artificial Sequence
<220> FEATURE:
<223> OTHER INFORMATION: chemically synthesized

<400> SEQUENCE: 168
ctcgctatcc                                                          10

<210> SEQ ID NO 169
<211> LENGTH: 10
<212> TYPE: DNA
<213> ORGANISM: Artificial Sequence
<220> FEATURE:
<223> OTHER INFORMATION: chemically synthesized

<400> SEQUENCE: 169
ggtgcacgtt                                                          10

<210> SEQ ID NO 170
<211> LENGTH: 10
<212> TYPE: DNA
<213> ORGANISM: Artificial Sequence
```

```
<220> FEATURE:
<223> OTHER INFORMATION: chemically synthesized

<400> SEQUENCE: 170
acacacgctg                                                              10

<210> SEQ ID NO 171
<211> LENGTH: 10
<212> TYPE: DNA
<213> ORGANISM: Artificial Sequence
<220> FEATURE:
<223> OTHER INFORMATION: chemically synthesized

<400> SEQUENCE: 171
ggtgaacgct                                                              10

<210> SEQ ID NO 172
<211> LENGTH: 10
<212> TYPE: DNA
<213> ORGANISM: Artificial Sequence
<220> FEATURE:
<223> OTHER INFORMATION: chemically synthesized

<400> SEQUENCE: 172
ccaacgtcgt                                                              10

<210> SEQ ID NO 173
<211> LENGTH: 10
<212> TYPE: DNA
<213> ORGANISM: Artificial Sequence
<220> FEATURE:
<223> OTHER INFORMATION: chemically synthesized

<400> SEQUENCE: 173
gatgccagac                                                              10

<210> SEQ ID NO 174
<211> LENGTH: 10
<212> TYPE: DNA
<213> ORGANISM: Artificial Sequence
<220> FEATURE:
<223> OTHER INFORMATION: chemically synthesized

<400> SEQUENCE: 174
gtccgtatgg                                                              10

<210> SEQ ID NO 175
<211> LENGTH: 10
<212> TYPE: DNA
<213> ORGANISM: Artificial Sequence
<220> FEATURE:
<223> OTHER INFORMATION: chemically synthesized

<400> SEQUENCE: 175
gaccaatgcc                                                              10

<210> SEQ ID NO 176
<211> LENGTH: 10
<212> TYPE: DNA
<213> ORGANISM: Artificial Sequence
<220> FEATURE:
<223> OTHER INFORMATION: chemically synthesized

<400> SEQUENCE: 176
gggccaatgt                                                              10
```

```
<210> SEQ ID NO 177
<211> LENGTH: 10
<212> TYPE: DNA
<213> ORGANISM: Artificial Sequence
<220> FEATURE:
<223> OTHER INFORMATION: chemically synthesized

<400> SEQUENCE: 177
gacgtggtga                                                            10

<210> SEQ ID NO 178
<211> LENGTH: 10
<212> TYPE: DNA
<213> ORGANISM: Artificial Sequence
<220> FEATURE:
<223> OTHER INFORMATION: chemically synthesized

<400> SEQUENCE: 178
gtggagtcag                                                            10

<210> SEQ ID NO 179
<211> LENGTH: 10
<212> TYPE: DNA
<213> ORGANISM: Artificial Sequence
<220> FEATURE:
<223> OTHER INFORMATION: chemically synthesized

<400> SEQUENCE: 179
tgagggtccc                                                            10

<210> SEQ ID NO 180
<211> LENGTH: 10
<212> TYPE: DNA
<213> ORGANISM: Artificial Sequence
<220> FEATURE:
<223> OTHER INFORMATION: chemically synthesized

<400> SEQUENCE: 180
agccgtggaa                                                            10

<210> SEQ ID NO 181
<211> LENGTH: 10
<212> TYPE: DNA
<213> ORGANISM: Artificial Sequence
<220> FEATURE:
<223> OTHER INFORMATION: chemically synthesized

<400> SEQUENCE: 181
aacgggcgtc                                                            10

<210> SEQ ID NO 182
<211> LENGTH: 10
<212> TYPE: DNA
<213> ORGANISM: Artificial Sequence
<220> FEATURE:
<223> OTHER INFORMATION: chemically synthesized

<400> SEQUENCE: 182
ggcaaaccct                                                            10

<210> SEQ ID NO 183
<211> LENGTH: 10
<212> TYPE: DNA
<213> ORGANISM: Artificial Sequence
<220> FEATURE:
<223> OTHER INFORMATION: chemically synthesized
```

<400> SEQUENCE: 183
acgagaggca                                                          10

<210> SEQ ID NO 184
<211> LENGTH: 10
<212> TYPE: DNA
<213> ORGANISM: Artificial Sequence
<220> FEATURE:
<223> OTHER INFORMATION: chemically synthesized

<400> SEQUENCE: 184
cttggcacga                                                          10

<210> SEQ ID NO 185
<211> LENGTH: 10
<212> TYPE: DNA
<213> ORGANISM: Artificial Sequence
<220> FEATURE:
<223> OTHER INFORMATION: chemically synthesized

<400> SEQUENCE: 185
tcttcggagg                                                          10

<210> SEQ ID NO 186
<211> LENGTH: 10
<212> TYPE: DNA
<213> ORGANISM: Artificial Sequence
<220> FEATURE:
<223> OTHER INFORMATION: chemically synthesized

<400> SEQUENCE: 186
aaggcacgag                                                          10

<210> SEQ ID NO 187
<211> LENGTH: 10
<212> TYPE: DNA
<213> ORGANISM: Artificial Sequence
<220> FEATURE:
<223> OTHER INFORMATION: chemically synthesized

<400> SEQUENCE: 187
cctcacgtcc                                                          10

<210> SEQ ID NO 188
<211> LENGTH: 10
<212> TYPE: DNA
<213> ORGANISM: Artificial Sequence
<220> FEATURE:
<223> OTHER INFORMATION: chemically synthesized

<400> SEQUENCE: 188
tcgcggaacc                                                          10

<210> SEQ ID NO 189
<211> LENGTH: 10
<212> TYPE: DNA
<213> ORGANISM: Artificial Sequence
<220> FEATURE:
<223> OTHER INFORMATION: chemically synthesized

<400> SEQUENCE: 189
ggcaaagctg                                                          10

<210> SEQ ID NO 190

```
<211> LENGTH: 10
<212> TYPE: DNA
<213> ORGANISM: Artificial Sequence
<220> FEATURE:
<223> OTHER INFORMATION: chemically synthesized

<400> SEQUENCE: 190
cctgttccct                                                          10

<210> SEQ ID NO 191
<211> LENGTH: 10
<212> TYPE: DNA
<213> ORGANISM: Artificial Sequence
<220> FEATURE:
<223> OTHER INFORMATION: chemically synthesized

<400> SEQUENCE: 191
gtgtcgagtc                                                          10

<210> SEQ ID NO 192
<211> LENGTH: 10
<212> TYPE: DNA
<213> ORGANISM: Artificial Sequence
<220> FEATURE:
<223> OTHER INFORMATION: chemically synthesized

<400> SEQUENCE: 192
tcagcacagg                                                          10

<210> SEQ ID NO 193
<211> LENGTH: 10
<212> TYPE: DNA
<213> ORGANISM: Artificial Sequence
<220> FEATURE:
<223> OTHER INFORMATION: chemically synthesized

<400> SEQUENCE: 193
tgtcctgcgt                                                          10

<210> SEQ ID NO 194
<211> LENGTH: 10
<212> TYPE: DNA
<213> ORGANISM: Artificial Sequence
<220> FEATURE:
<223> OTHER INFORMATION: chemically synthesized

<400> SEQUENCE: 194
accacgcctt                                                          10

<210> SEQ ID NO 195
<211> LENGTH: 10
<212> TYPE: DNA
<213> ORGANISM: Artificial Sequence
<220> FEATURE:
<223> OTHER INFORMATION: chemically synthesized

<400> SEQUENCE: 195
gagtcctcac                                                          10

<210> SEQ ID NO 196
<211> LENGTH: 10
<212> TYPE: DNA
<213> ORGANISM: Artificial Sequence
<220> FEATURE:
<223> OTHER INFORMATION: chemically synthesized

<400> SEQUENCE: 196
```
aacccttccc          10

<210> SEQ ID NO 197
<211> LENGTH: 10
<212> TYPE: DNA
<213> ORGANISM: Artificial Sequence
<220> FEATURE:
<223> OTHER INFORMATION: chemically synthesized

<400> SEQUENCE: 197
agttccgcga          10

<210> SEQ ID NO 198
<211> LENGTH: 10
<212> TYPE: DNA
<213> ORGANISM: Artificial Sequence
<220> FEATURE:
<223> OTHER INFORMATION: chemically synthesized

<400> SEQUENCE: 198
gttgcgcagt          10

<210> SEQ ID NO 199
<211> LENGTH: 10
<212> TYPE: DNA
<213> ORGANISM: Artificial Sequence
<220> FEATURE:
<223> OTHER INFORMATION: chemically synthesized

<400> SEQUENCE: 199
tgacagcccc          10

<210> SEQ ID NO 200
<211> LENGTH: 10
<212> TYPE: DNA
<213> ORGANISM: Artificial Sequence
<220> FEATURE:
<223> OTHER INFORMATION: chemically synthesized

<400> SEQUENCE: 200
tctgcctgga          10

<210> SEQ ID NO 201
<211> LENGTH: 100
<212> TYPE: DNA
<213> ORGANISM: Artificial Sequence
<220> FEATURE:
<223> OTHER INFORMATION: chemically synthesized

<400> SEQUENCE: 201
agttcttccg tagctgattc gattcgatcg agctacgttc gatcgatacg ctagctcata    60
ctggccctag cttagcttac taacttagga ttagtagctc                         100

<210> SEQ ID NO 202
<211> LENGTH: 100
<212> TYPE: DNA
<213> ORGANISM: Artificial Sequence
<220> FEATURE:
<223> OTHER INFORMATION: chemically synthesized

<400> SEQUENCE: 202
tcaagaaggc atcgactaag ctaagctagc tcgatgcaag ctagctatgc gatcgagtat    60
gaccgggatc gaatcgaatg attgaatcct aatcatcgag                         100

<210> SEQ ID NO 203
<211> LENGTH: 100
<212> TYPE: DNA
<213> ORGANISM: Artificial Sequence
<220> FEATURE:
<223> OTHER INFORMATION: chemically synthesized

<400> SEQUENCE: 203
tgccatacga agttcagcat cgctatcgtg tctagcatca tagctctacg actacagact    60
ttagctacgt acgactgatg catccgacta gctctagcta                         100

<210> SEQ ID NO 204
<211> LENGTH: 100
<212> TYPE: DNA
<213> ORGANISM: Artificial Sequence
<220> FEATURE:
<223> OTHER INFORMATION: chemically synthesized

<400> SEQUENCE: 204
acggtatgct tcaagtcgta gcgatagcac agatcgtagt atcgagatgc tgatgtctga    60
aatcgatgca tgctgactac gtaggctgat cgagatcgat                         100

<210> SEQ ID NO 205
<211> LENGTH: 15
<212> TYPE: DNA
<213> ORGANISM: Artificial Sequence
<220> FEATURE:
<223> OTHER INFORMATION: chemically synthesized

<400> SEQUENCE: 205
acgaagttca gcatc                                                     15

<210> SEQ ID NO 206
<211> LENGTH: 15
<212> TYPE: DNA
<213> ORGANISM: Artificial Sequence
<220> FEATURE:
<223> OTHER INFORMATION: chemically synthesized

<400> SEQUENCE: 206
gtagctgatt cgatt                                                     15

<210> SEQ ID NO 207
<211> LENGTH: 15
<212> TYPE: DNA
<213> ORGANISM: Artificial Sequence
<220> FEATURE:
<223> OTHER INFORMATION: chemically synthesized

<400> SEQUENCE: 207
attctggtat gctag                                                     15

<210> SEQ ID NO 208
<211> LENGTH: 15
<212> TYPE: DNA
<213> ORGANISM: Artificial Sequence
<220> FEATURE:
<223> OTHER INFORMATION: chemically synthesized

<400> SEQUENCE: 208
ataatccgta gctat                                                     15

<210> SEQ ID NO 209
<211> LENGTH: 15

-continued

```
<212> TYPE: DNA
<213> ORGANISM: Artificial Sequence
<220> FEATURE:
<223> OTHER INFORMATION: chemically synthesized

<400> SEQUENCE: 209
taagctaggg ccagt                                                        15

<210> SEQ ID NO 210
<211> LENGTH: 15
<212> TYPE: DNA
<213> ORGANISM: Artificial Sequence
<220> FEATURE:
<223> OTHER INFORMATION: chemically synthesized

<400> SEQUENCE: 210
atgatccatg ttact                                                        15

<210> SEQ ID NO 211
<211> LENGTH: 15
<212> TYPE: DNA
<213> ORGANISM: Artificial Sequence
<220> FEATURE:
<223> OTHER INFORMATION: chemically synthesized

<400> SEQUENCE: 211
gatctttagc tagtc                                                        15

<210> SEQ ID NO 212
<211> LENGTH: 15
<212> TYPE: DNA
<213> ORGANISM: Artificial Sequence
<220> FEATURE:
<223> OTHER INFORMATION: chemically synthesized

<400> SEQUENCE: 212
agtcgtacgt agcta                                                        15
```

POLYNUCLEOTIDE ANALYSIS USING COMBINATORIAL PCR

This application is a national stage filing under 35 U.S.C. 371 of International Application No. PCT/GB02/01489, filed Mar. 28, 2002, which claims priority from United Kingdom Patent Application No.0108182.7, filed Apr. 2, 2001, the specifications of both of which are incorporated by reference herein. International Application No. PCT/GB02/01489 was published under PCT Article 21(2) in English.

This invention relates to methods and apparatus for analysis of biological materials. In particular the invention relates to methods and apparatus for the analysis of DNA and RNA using the polymerase chain reaction (PCR).

The polymerase chain reaction is a technique which is well known to those skilled in the art of biochemical research, is widely used for isolation and analysis of biological samples and is described in many publications, for example "PCR" by C. R. Newton and A. Graham, published by Bios scientific publishers, Oxford 1997.

In general, the polymerase chain reaction makes use of two or more oligonucleotides which serve as primers for a primer-dependent DNA polymerase enzyme. This enzyme is used to produce multiple copies of double-stranded DNA molecules present in an analyte. By selection of suitable primers matching specific regions of the target DNA, selective amplification of those regions may be effected by repetitive cycling of the reaction mixture through a temperature profile which includes the steps of denaturing of double-stranded DNA, annealing of oligonucleotide primers to the denaturated template DNA and primer extension using a thermostable DNA polymerase.

The use of oligonucleotides immobilised on solid supports as primers for PCR has been described in a number of documents. For example, U.S. Pat. No. 5,656,462 describes a method of synthesising a polynucleotide immobilised support on PCR microplates, and World Patent No. WO 9932654 describes a method for performing RT-PCR on oligonucleotide-immobilised PCR microplates. In both these patent documents, the same oligonucleotide is immobilised on the surface of all the wells of the microplate in order to allow parallel processing of multiple samples of analytes.

U.S. Pat. No. 5,770,358 describes the use of PCR to amplify oligonucleotide "tags" bound to a solid-support bead in order to discriminate between different populations of such beads.

U.S. Pat. No. 5,916,776 describes a method for amplification of a target nucleic acid in which copies of a first strand are captured on a solid support at a first location and moved to a second location at which copies of the first strand are regenerated. Procedures for practising the method by use of magnetic particles and microfluidic devices are also disclosed. A further microfluidic device is described by the same applicants in U.S. Pat. No. 5,939,291.

SUMMARY OF THE INVENTION

The present invention provides processes and apparatus for analysis of DNA molecules by a combinatorial method which makes use of multiple oligonucleotide primers immobilised on solid supports.

Advantageously, the present invention provides a method and apparatus for analysis of DNA samples which requires no prior knowledge of the sequence information contained in the sample DNA, provides a large volume of data from a single experiment, and uses standard components and materials and is capable of mass-production.

According to the present invention, there is provided a process for transcription or amplification of sequence information from genetic material by chain extension of oligonucleotide primers characterised in that during the performance of the process:

(i) at least two oligonucleotide primers are in solution, and (ii) at least two other oligonucleotide primers are attached to solid supports, and (iii) the nucleotide-sequence of at least one solid-support-bound oligonucleotide is partially or completely identical with or complementary to the nucleotide-sequence of at least one oligonucleotide in solution.

The present invention further provides a process for transcription or amplification of sequence information from a polynucleotide by chain extension of oligonucleotide primers characterised in that during the performance of the process:

(i) at least two oligonucleotide primers are in solution, and (ii) at least one other oligonucleotide primer is attached to a solid support, and (iii) the nucleotide-sequence of at least one solid-support-bound oligonucleotide is partially or completely identical with or complementary to part of the nucleotide-sequence of the polynucleotide.

The present invention further provides an apparatus for the analysis of analytes which comprises a multiplicity of solid support surfaces, a multiplicity of oligonucleotides or polynucleotides attached to said solid support surfaces, such that each surface bears a single oligonucleotide or polynucleotide, identification means allowing each of said solid-support surfaces to be distinguished from other solid support surfaces, containment means allowing said solid-support surfaces to be contacted with solutions of analytes, enzymes or reagents, and closure means to allow agitation, heating or cooling without leakage.

The invention further provides an apparatus for the analysis of analytes which comprises a single solid support surface segregated into zones, a multiplicity of oligonucleotides or polynucleotides attached to said zones, such that each zone bears a single oligonucleotide or polynucleotide, identification means allowing each of said zones to be distinguished from other zones, containment means allowing said solid-support surface to be contacted with solutions of analytes, enzymes or reagents, and closure means to allow agitation, heating or cooling without leakage.

The invention further provides an apparatus as hereinbefore defined further comprising containment means allowing any individual solid-support surface to be contacted with a specific analyte, enzyme or reagent without so contacting other solid-support surfaces, such that a different analyte, enzyme or reagent may be contacted with every individual solid-support surface.

The invention further provides apparatus as hereinbefore defined in which each solid support-surface or zone of said surface bears multiple oligonucleotides or polynucleotides in combination, such that each said surface or zone bears a different combination of oligonucleotides or polynucleotides, said combination comprising a sub-set of the totality of oligonucleotides or polynucleotides attached to all said surfaces or zones of the apparatus.

The invention further provides apparatus comprising a single solid support surface segregated into zones as hereinbefore defined further comprising division means allowing each of said zones to be physically separated from other zones, thereby enabling the entire support surface to be physically divided into individual zones.

The invention further provides a process for the preparation of multiple polynucleotides attached to a plurality of support surfaces which comprises the steps of:

(i) providing a plurality of support surfaces (ii) covalently linking one or more oligonucleotides to each of said surfaces by means of a stable linker moiety covalently linked to the 5'-terminus of each oligonucleotide and covalently linked to the support surface, such that each of said surfaces bears a different oligonucleotide or combination of oligonucleotides, (iii) contacting each of said support surfaces with one or more additional oligonucleotides and a nucleic acid or mixture of nucleic acids in the presence of an enzyme or enzymes together with enzyme substrates and co-factors so as to transfer genetic sequence data from the nucleic acid or mixture of nucleic acids to the oligonucleotides of the support surface, (iv) optionally heating or altering the pH of said solid-supported oligonucleotide or oligonucleotides, mixture of oligonucleotides and nucleic acids, enzyme or enzymes, substrates and co-factors so as to effect dissociation of double-stranded molecules, (v) optionally cooling or altering the pH of said solid-supported oligonucleotide or oligonucleotides, mixture of oligonucleotides and nucleic acids, enzyme or enzymes, substrates and co-factors so as to effect further transfer of genetic sequence data from the nucleic acid or mixture of nucleic acids to the oligonucleotides of the support surface, and (vi) optionally repeating steps (iv) to (v) one or more times in a cyclic manner, so as to effect conversion of individual oligonucleotides of the support surface to polynucleotides containing genetic sequence data derived from the nucleic acid or mixture of nucleic acids.

The invention further provides a process for the preparation of multiple polynucleotides attached to a support surface which comprises the steps of:

(i) providing a support surface (ii) segregating the surface into discrete zones (iii) covalently linking a plurality of oligonucleotides to said zones by means of a stable linker moiety covalently linked to the 5'-terminus of each oligonucleotide and covalently linked to the support surface, such that each individual zone bears a different oligonucleotide or combination of oligonucleotides, (iv) contacting said support surface with one or more additional oligonucleotides and a nucleic acid or mixture of nucleic acids in the presence of an enzyme or enzymes together with enzyme substrates and co-factors so as to transfer genetic sequence data from the nucleic acid or mixture of nucleic acids to the oligonucleotides of the support surface, (v) optionally heating or altering the pH of said solid-support-bound oligonucleotide or oligonucleotides, mixture of oligonucleotides and nucleic acids, enzyme or enzymes, substrates and co-factors so as to effect dissociation of double-stranded molecules, (vi) optionally cooling or altering the pH of said solid-support-bound oligonucleotide or oligonucleotides, mixture of oligonucleotides and nucleic acids, enzyme or enzymes, substrates and co-factors so as to effect further transfer of genetic sequence data from the nucleic acid or mixture of nucleic acids to the oligonucleotides of the support surface, and (vii) optionally repeating steps (v) to (vi) one or more times in a cyclic manner, so as to effect conversion of individual oligonucleotides of the support surface to polynucleotides containing genetic sequence data derived from the nucleic acid or mixture of nucleic acids.

The invention further provides a process for the analysis of a nucleic acid or mixture of nucleic acids which comprises the steps of:

(i) applying the process as hereinbefore defined in order to produce a support surface or plurality of support surfaces bearing multiple polynucleotides containing genetic sequence data derived from the nucleic acid or mixture of nucleic acids, (ii) contacting at least one of said support surfaces with one or more oligonucleotide or polynucleotide probes capable of hybridising to polynucleotides of the support surface or surfaces, (iii) washing the support surface or surfaces to remove unhybridised oligonucleotide or polynucleotide probes, (iv) measuring the quantity of oligonucleotide or polynucleotide probe hybridised to each polynucleotide of the support surface or surfaces, and (v) optionally washing the support surface or surfaces under conditions sufficient to remove hybridised oligonucleotide or polynucleotide probes and repeating steps (ii) to (iv) one or more times using a different oligonucleotide or polynucleotide probe or probes in each iteration.

The invention further provides a process for the analysis of a nucleic acid or mixture of nucleic acids which comprises the steps of:

(i) applying the process as hereinbefore defined in order to produce a support surface or plurality of support surfaces bearing multiple polynucleotides containing genetic sequence data derived from the nucleic acid or mixture of nucleic acids, (ii) contacting at least one of said support surfaces with one or more oligonucleotide primers in the presence of an enzyme or enzymes together with enzyme substrates and co-factors so as to produce one or more polynucleotides complementary to the polynucleotides of the support surface or surfaces, (iii) optionally heating or altering the pH of said support surface or surfaces, oligonucleotide primer or primers, enzyme or enzymes, substrates and co-factors so as to effect dissociation of double-stranded molecules, (iv) optionally cooling or altering the pH of said support surface or surfaces, oligonucleotide primer or primers, enzyme or enzymes, substrates and co-factors so as to produce further polynucleotides complementary to the polynucleotides of the support surface or surfaces, (v) optionally repeating steps (iii) to (iv) one or more times in a cyclic manner, so as to effect conversion of the primer oligonucleotide or oligonucleotides to polynucleotides complementary to the polynucleotides of the support surface or surfaces, (vi) hybridising said complementary polynucleotides to the polynucleotides of the support surface or surfaces, (vii) washing the support surface or surfaces to remove unhybridised polynucleotides, (viii) measuring the quantity of complementary polynucleotide hybridised to each polynucleotide of the support surface or surfaces, and (ix) optionally washing the support surface or surfaces under conditions sufficient to remove hybridised complementary polynucleotides and repeating steps (ii) to (viii) one or more times using a different oligonucleotide primer or primers in each iteration.

The invention further provides a process for the analysis of a nucleic acid or mixture of nucleic acids which comprises the steps of:

(i) providing a multiplicity of support surfaces each equipped with unique identification means, (ii) covalently linking each of a set of n oligonucleotides, where n is an integral number greater than unity, to one of said support surfaces by means of a stable linker moiety covalently linked to the 5'-terminus of each oligonucleotide and covalently linked to the support surface, such that each individual oligonucleotide is attached to an individual support surface, (iii) contacting all of said support-surfaces with a solution containing a mixture of all n oligonucleotides and the nucleic acid or mixture of nucleic acids to be analysed in the presence of an enzyme or enzymes together with enzyme substrates and co-factors so as to transfer genetic sequence data from the nucleic acid or mixture of nucleic acids to the oligonucleotides bound to the support surfaces, (iv) optionally heating or altering the pH of said support surfaces, mixture of oligonucleotides and nucleic acids, enzyme or enzymes, substrates and co-factors so as to effect dissociation of double-stranded molecules, (v) optionally cooling or altering the pH of said support surfaces, mixture of oligonucleotides and nucleic acids, enzyme or enzymes, substrates and co-factors so as to effect further transfer of genetic sequence data from the nucleic acid or mixture of nucleic acids to the oligonucleotides of the support surface, (vi) optionally repeating steps (iv) and (v) one or more times in a cyclic manner, so as to produce n sets of support-bound polynucleotides by effecting conversion of individual support-bound oligonucleotides to polynucleotides containing genetic sequence data derived from the mixtures of nucleic acids, (vii) washing said support surfaces under denaturing conditions to denature double-stranded molecules and remove oligonucleotides or polynucleotides hybridised to said support-bound polynucleotides, (viii) contacting one or more of said n support surfaces with a solution containing one of said n oligonucleotide primers in the presence of an enzyme or enzymes together with enzyme substrates and co-factors so as to produce polynucleotides complementary to the polynucleotides bound to said support surfaces, (ix) optionally heating or altering the pH of said support surfaces, oligonucleotide primers, enzyme or enzymes, substrates and co-factors so as to effect dissociation of double-stranded molecules, (x) optionally cooling or altering the pH of said support surfaces, oligonucleotide primers, enzyme or enzymes, substrates and co-factors so as to produce further polynucleotides complementary to the polynucleotides bound to said support surfaces, (xi) optionally repeating steps (ix) to (x) one or more times in a cyclic manner, so as to effect conversion of the primer oligonucleotide to polynucleotides complementary to the polynucleotides bound to said support surfaces, (xii) hybridising said complementary polynucleotides to the polynucleotides bound to said support surfaces, (xiii) washing said support surfaces under non-denaturing conditions to remove unhybridised polynucleotides, (xiv) separating each of said support surfaces from other support surfaces, (xv) washing each of said support surfaces under denaturing conditions to denature double-stranded molecules and release hybridised polynucleotides into solution, (xvi) analysing the hybridised polynucleotides released into solution from each said support surface, and (xvii) optionally repeating steps (viii) to (xvi) one or more times using a different member of the said set of n oligonucleotide primers in each iteration.

The invention further provides a process for the analysis of a nucleic acid or mixture of nucleic acids which comprises the steps of:

(i) providing a multiplicity of support surfaces each equipped with unique identification means, (ii) covalently linking each of a set of n oligonucleotides, where n is an integral number greater than unity, to one of said support surfaces by means of a stable linker moiety covalently linked to the 5'-terminus of each oligonucleotide and covalently linked to the support surface, such that each individual oligonucleotide is attached to an individual support surface, (iii) contacting all of said support-surfaces with a solution containing a mixture of all n oligonucleotides and the nucleic acid or mixture of nucleic acids to be analysed in the presence of an enzyme or enzymes together with enzyme substrates and co-factors so as to transfer genetic sequence data from the nucleic acid or mixture of nucleic acids to the oligonucleotides bound to the support surfaces, (iv) optionally heating or altering the pH of said support surfaces, mixture of oligonucleotides and nucleic acids, enzyme or enzymes, substrates and co-factors so as to effect dissociation of double-stranded molecules, (v) optionally cooling or altering the pH of said support surfaces, mixture of oligonucleotides and nucleic acids, enzyme or enzymes, substrates and co-factors so as to effect further transfer of genetic sequence data from the nucleic acid or mixture of nucleic acids to the oligonucleotides of the support surface, (vi) optionally repeating steps (iv) and (v) one or more times in a cyclic manner, so as to produce n sets of support-bound polynucleotides by effecting conversion of individual support-bound oligonucleotides to polynucleotides containing genetic sequence data derived from the mixtures of nucleic acids, (vii) washing said support surfaces under denaturing conditions to denature double-stranded molecules and remove oligonucleotides or polynucleotides hybridised to said support-bound polynucleotides, (viii) individually contacting each of said n support surfaces with a solution containing one of said n oligonucleotide primers in the presence of an enzyme or enzymes together with enzyme substrates and co-factors so as to produce polynucleotides complementary to the polynucleotides bound to said support surface, such that every one of said n support surfaces is contacted with a unique member of the set of n oligonucleotide primers, (ix) optionally heating or altering the pH of every said support surface, oligonucleotide primer, enzyme or enzymes, substrates and co-factors so as to effect dissociation of double-stranded molecules, (x) optionally cooling or altering the pH of every said support surface, oligonucleotide primer, enzyme or enzymes, substrates and co-factors so as to produce further polynucleotides complementary to the polynucleotides bound to said support surface, (xi) optionally repeating steps (ix) to (x) one or more times in a cyclic manner, so as to effect conversion of the primer oligonucleotide to polynucleotides complementary to the polynucleotides bound to said support surface, (xii) hybridising said complementary polynucleotides to the polynucleotides bound to said support surface, (xiii) washing said support surface under non-denaturing conditions to remove unhybridised polynucleotides, (xiv) washing said support surface under denaturing conditions to denature double-stranded molecules and release hybridised polynucleotides into solution, (xv) analysing the hybridised polynucleotides released into solution from each said support surface, and (xvi) optionally repeating steps (viii) to (xv) one or more times using for each of said n support surfaces a different member of the said set of n oligonucleotide primers in each iteration.

The invention further provides a process for the analysis of a nucleic acid or mixture of nucleic acids which comprises the steps of:

(i) providing a support surface, (ii) segregating the surface into n discrete zones, where n is an integral number greater than unity, (iii) providing each of said zones with unique identification means, (iv) covalently linking each of a set of n oligonucleotides to one of said zones by means of a stable linker moiety covalently linked to the 5'-terminus of each oligonucleotide and covalently linked to the support surface, such that each individual oligonucleotide is attached to an individual zone of the support surface, (v) contacting said support-surface with a solution containing a mixture of all n oligonucleotides and the nucleic acid or mixture of nucleic acids to be analysed in the presence of an enzyme or enzymes together with enzyme substrates and co-factors so as to transfer genetic sequence data from the nucleic acid or mixture of nucleic acids to the oligonucleotides attached to the support surface, (vi) optionally heating or altering the pH of said support surface, mixture of oligonucleotides and nucleic acids, enzyme or enzymes, substrates and co-factors so as to effect dissociation of double-stranded molecules, (vii) optionally cooling or altering the pH of said support surface, mixture of oligonucleotides and nucleic acids, enzyme or enzymes, substrates and co-factors so as to effect further transfer of genetic sequence data from the nucleic acid or mixture of nucleic acids to the oligonucleotides of the support surface, (viii) optionally repeating steps (vi) and (vii) one or more times in a cyclic manner, so as to produce n sets of support-bound polynucleotides by effecting conversion of individual support-bound oligonucleotides to polynucleotides containing genetic sequence data derived from the mixtures of nucleic acids, (ix) washing said support zones under denaturing conditions to denature double-stranded molecules and remove oligonucleotides or polynucleotides hybridised to said support-bound polynucleotides, (x) contacting one or more of said n support zones with a solution containing one of said n oligonucleotide primers in the presence of an enzyme or enzymes together with enzyme substrates and co-factors so as to produce polynucleotides complementary to the polynucleotides bound to said support zones, (xi) optionally heating or altering the pH of said support zones, oligonucleotide primer, enzyme or enzymes, substrates and co-factors so as to effect dissociation of double-stranded molecules, (xii) optionally cooling or altering the pH of said support zones, oligonucleotide primer, enzyme or enzymes, substrates and co-factors so as to produce further polynucleotides complementary to the polynucleotides bound to said support zones, (xiii) optionally repeating steps (xi) to (xii) one or more times in a cyclic manner, so as to effect conversion of the primer oligonucleotide to polynucleotides complementary to the polynucleotides bound to said support zones, (xiv) hybridising said complementary polynucleotides to the polynucleotides bound to said support zones, (xv) washing said support zones under non-denaturing conditions to remove unhybridised polynucleotides, (xvi) separating each of said support zones from other support zones, (xvii) washing each said support zone under denaturing conditions to denature double-stranded molecules and release hybridised polynucleotides into solution, (xviii) analysing the hybridised polynucleotides released into solution from each said support zone, and (xix) optionally repeating steps (x) to (xviii) one or more times using in each iteration a solution of a different oligonucleotide primer selected from the set of n oligonucleotide primers.

The invention further provides a process for the analysis of a nucleic acid or mixture of nucleic acids which comprises the steps of:

(i) providing a support surface, (ii) segregating the surface into n discrete zones, where n is an integral number greater than unity, (iii) providing each of said zones with unique identification means, (iv) covalently linking each of a set of n oligonucleotides to one of said zones by means of a stable linker moiety covalently linked to the 5'-terminus of each oligonucleotide and covalently linked to the support surface, such that each individual oligonucleotide is attached to an individual zone of the support surface, (v) contacting said support-surface with a solution containing a mixture of all n oligonucleotides and the nucleic acid or mixture of nucleic acids to be analysed in the presence of an enzyme or enzymes together with enzyme substrates and co-factors so as to transfer genetic sequence data from the nucleic acid or mixture of nucleic acids to the oligonucleotides attached to the support surface, (vi) optionally heating or altering the pH of said support surface, mixture of oligonucleotides and nucleic acids, enzyme or enzymes, substrates and co-factors so as to effect dissociation of double-stranded molecules, (vii) optionally cooling or altering the pH of said support surface, mixture of oligonucleotides and nucleic acids, enzyme or enzymes, substrates and co-factors so as to effect further transfer of genetic sequence data from the nucleic acid or mixture of nucleic acids to the oligonucleotides of the support surface, (viii) optionally repeating steps (vi) and (vii) one or more times in a cyclic manner, so as to produce n sets of support-bound polynucleotides by effecting conversion of individual support-bound oligonucleotides to polynucleotides containing genetic sequence data derived from the mixtures of nucleic acids, (ix) washing said support surface under denaturing conditions to denature double-stranded molecules and remove oligonucleotides or polynucleotides hybridised to said support-bound polynucleotides, (x) physically dividing the support surface to form n individually-identifiable support zones each bearing a set of support-bound polynucleotides derived by extension of one of the n support-bound oligonucleotide primers, (xi) individually contacting every one of said n support zones with a solution containing one of said n oligonucleotide primers in the presence of an enzyme or enzymes together with enzyme substrates and co-factors so as to produce polynucleotides complementary to the polynucleotides bound to said support zone, such that every one of said n support zones is contacted with a unique member of the set of n oligonucleotide primers, (xii) optionally heating or altering the pH of every said support zone, oligonucleotide primer, enzyme or enzymes, substrates and co-factors so as to effect dissociation of double-stranded molecules, (xiii) optionally cooling or altering the pH of every said support zone, oligonucleotide primer, enzyme or enzymes, substrates and co-factors so as to produce further polynucleotides complementary to the polynucleotides bound to said support zone, (xiv) optionally repeating steps (xii) to (xiii) one or more times in a cyclic manner, so as to effect conversion of the primer oligonucleotide to polynucleotides complementary to the polynucleotides bound to said support zone, (xv) hybridising said complementary polynucleotides to the polynucleotides bound to said support zone, (xvi) washing said support zone under non-denaturing conditions to remove unhybridised polynucleotides, (xvii) washing said support zone under denaturing conditions to denature double-stranded molecules and release hybridised polynucleotides into solution, (xviii) analysing the hybridised polynucleotides released into solution from each said support zone, and (xix) optionally repeating steps (xi) to (xviii) one or more times using for each of said n support zones a different member of the said set of n oligonucleotide primers in each iteration.

The invention further provides a process for the analysis of two or more distinct mixtures of nucleic acids which comprises the steps of:

(i) applying the processes as hereinbefore defined in order to produce a set of support surfaces or zones bearing a first set of immobilised polynucleotides containing genetic sequence data derived from a first mixture of nucleic acids, together with a first set of polynucleotides complementary to said first set of immobilised polynucleotides, (ii) applying the processes as hereinbefore defined in order to produce a set of support surfaces or zones bearing a second set of immobilised polynucleotides containing genetic sequence data derived from a second mixture of nucleic acids, together with a second set of polynucleotides complementary to said second set of immobilised polynucleotides, (iii) hybridising said first set of complementary polynucleotides to said first set of immobilised polynucleotides, (iv) individually releasing and analysing the complementary polynucleotides hybridised to each of said first set of immobilised polynucleotides, (v) hybridising said second set of complementary polynucleotides to said second set of immobilised polynucleotides (vi) individually releasing and analysing the complementary polynucleotides hybridised to each of said second set of immobilised polynucleotides, (vii) optionally hybridising one or more members of said first set of complementary polynucleotides to one or more members of said second set of immobilised polynucleotides, individually releasing and analysing the complementary polynucleotides hybridised to each of said second set of immobilised polynucleotides, (viii) optionally hybridising one or more members of said second set of complementary polynucleotides to one or more members of said first set of immobilised polynucleotides, individually releasing and analysing the complementary polynucleotides hybridised to each of said first set of immobilised polynucleotides, and (ix) optionally repeating steps (ii) and (v) to (viii) for further mixtures of nucleic acids.

The invention further provides a process as hereinbefore defined in which a single support surface segregated into zones is physically divided into discrete zones after completing at least one step of the process and each such zone is processed separately during subsequent steps of the process.

The invention further provides a process as hereinbefore defined in which the stable linker moiety is covalently linked to the 5'-terminus of each oligonucleotide by means of covalent bonding to one or more atoms of the carbohydrate moiety of the 5'-terminal nucleotide.

The invention further provides a process as hereinbefore defined in which the stable linker moiety is covalently linked to the 5'-terminus of each oligonucleotide by means of covalent bonding to one or more atoms of the heterocyclic moiety of the 5'-terminal nucleotide. The invention further provides a process as hereinbefore defined in which the stable linker moiety comprises a covalently-bound functionality with a chemical equivalence of between 100 and 5000 picomoles per square millimeter of support surface.

The invention further provides a process as hereinbefore defined in which the stable linker moiety is thermally stable in aqueous solution at 95 deg. C.

The invention further provides a process as hereinbefore defined in which the stable linker moiety is hydrolytically stable in aqueous solution between pH 4 and pH 11.

The invention further provides a process as hereinbefore defined in which the oligonucleotides contain internucleotide linkages selected from the group comprising phosphodiesters, phosphorothioates and methyl phosphonates.

The invention further provides a process as hereinbefore defined in which one or more oligonucleotides contain labelled molecules selected from the group comprising fluorescent molecules, luminescent molecules, biotin-labelled molecules, radiolabelled molecules and enzyme conjugates.

The invention further provides a process as hereinbefore defined in which the nucleic acid or mixture of nucleic acids to be analysed is selected from the group comprising single-stranded DNA molecules, double-stranded DNA molecules and messenger RNA molecules.

The invention further provides a process as hereinbefore defined in which the enzyme or enzymes are selected from the group comprising DNA polymerases, thermostable DNA polymerases, reverse transcriptases, thermostable reverse transcriptases, DNA ligases and thermostable DNA ligases.

The invention further provides a process as hereinbefore defined in which the enzyme substrates and co-factors are selected from the group comprising nucleoside triphosphates, fluorescent nucleoside triphosphates, luminescent nucleoside triphosphates, biotin-labelled nucleoside triphosphates, amino-allyl nucleoside triphosphates, radiolabelled nucleoside triphosphates, metal salts, buffering agents, chelating agents, chaotropic agents and nuclease inhibitors.

The invention further provides an apparatus as hereinbefore defined in which the support surface, containment means and closure means comprise separate components adapted to be assembled to form the apparatus.

The invention further provides an apparatus as hereinbefore defined in which each set of immobilised oligonucleotides or polynucleotides further comprises control substances or indicia adapted for identification, alignment or calibration purposes.

The invention further provides apparatus and processes as hereinbefore defined further comprising automated handling equipment allowing high-throughput analysis of DNA samples under computer control.

The invention further provides a computer program comprising software code portions for controlling apparatus adapted to perform the process of the invention as hereinbefore defined.

The invention further provides a computer program comprising software code portions for predicting the outcome of the process of the invention as hereinbefore defined for any given combination of oligonucleotides in relation to the presence or absence in an analyte of one or more polynucleotides.

BRIEF DESCRIPTION OF THE DRAWINGS

Specific embodiments of the invention will now be described, by way of example, with reference to the accompanying drawings, in which:—

FIG. 17 shows a table of oligonucleotide sequences which may be used in the practice of the invention.

FIG. 18 shows schematically a process for distinguishing between two DNA samples by practising the process of the invention.

DETAILED DESCRIPTION OF THE INVENTION

Figure 1:
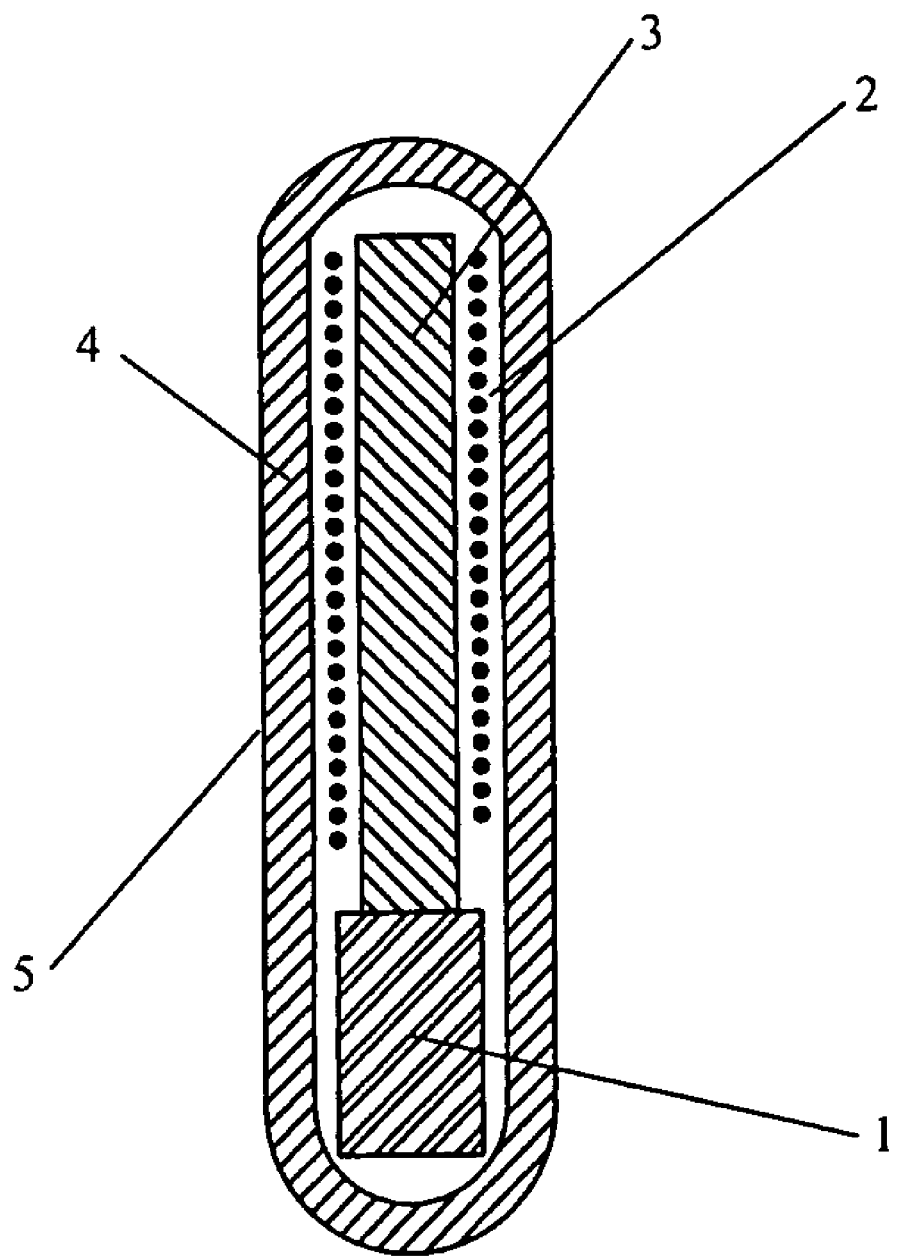
FIG. 1 shows a radio-frequency transponder sealed in a glass envelope whose surface may be used as a solid support surface in the practice of the invention.

In a preferred embodiment of the apparatus of the invention, the support surface is the external glass surface of a radio-frequency tag (RF tag) as illustrated in FIG. 1. Referring to the drawing, this consists of a microelectronic radio-frequency transponder circuit 1 equipped with an antenna coil 2 wound on a ferrite core 3. The entire assembly is hermetically sealed in a glass envelope 4 whose outer surface 5 serves as the support surface for immobilised oligonucleotides in the practice of the invention.

Figure 2:
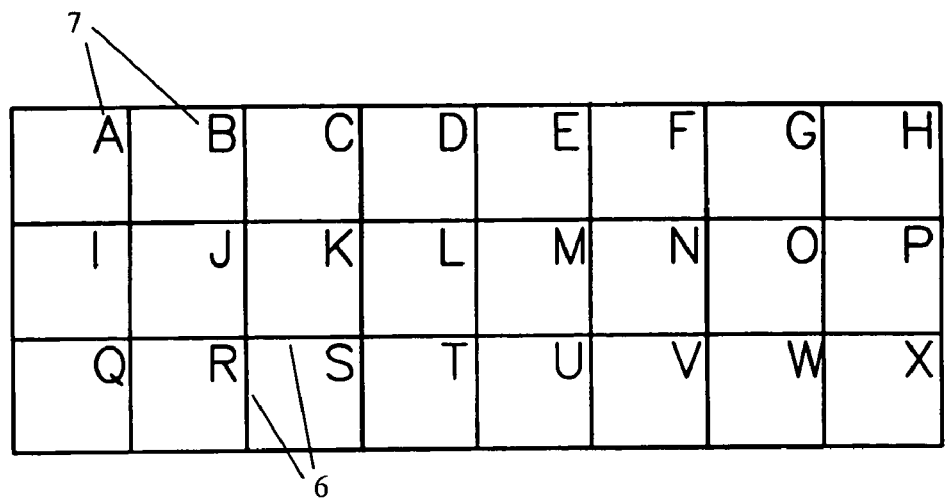
FIG. 2 shows a glass plate divided into zones which may be used as a solid support surface in the practice of the invention.

In a second preferred embodiment of the apparatus of the invention, the support surface is the surface of a glass plate divided into zones as illustrated in FIG. 2. Referring to the drawing, the surface of the glass plate is divided into zones by means of a grid of lines 6 which are scribed into the surface, for example by use of a glass knife or a diamond pencil, or etched into the surface by chemical treatment, for example with hydrofluoric acid, or by laser ablation. Zones are also equipped with unique identifying marks 7.

Figure 3:
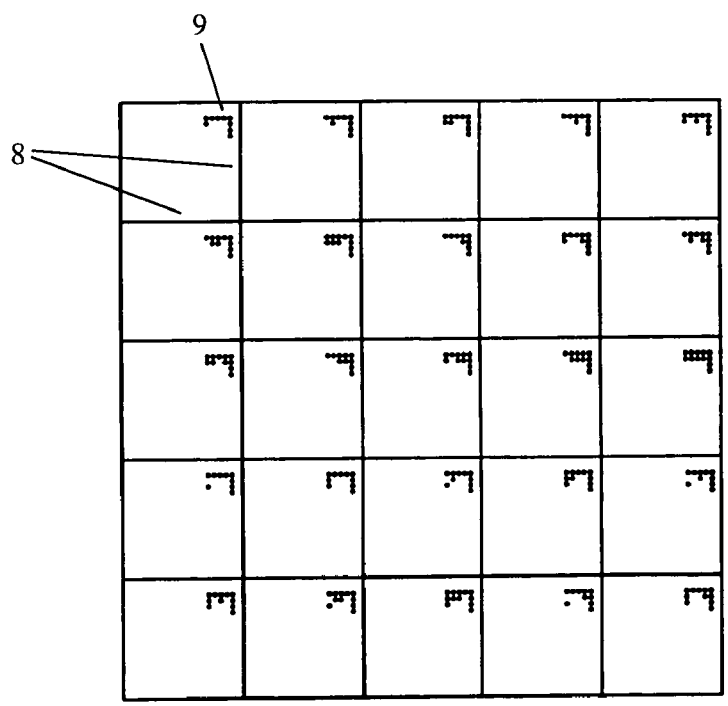
FIG. 3 shows a silicon wafer divided into zones which may be used as a solid support surface in the practice of the invention.

In a third preferred embodiment of the apparatus of the invention, the support surface is the surface of a silicon wafer divided into zones as illustrated in FIG. 3. Referring to the drawing, the surface of the silicon wafer is divided into zones by means of a grid of lines 8 which are formed in the surface, for example by laser ablation. Zones are also equipped with unique identifying marks 9 in the form of a two-dimensional bar code formed by laser ablation. Prior to use of the wafer as a solid-support for oligonucleotide immobilisation, a layer of silicon oxide is formed on the surface of the wafer using standard microelectronic fabrication methods.

Figure 4:
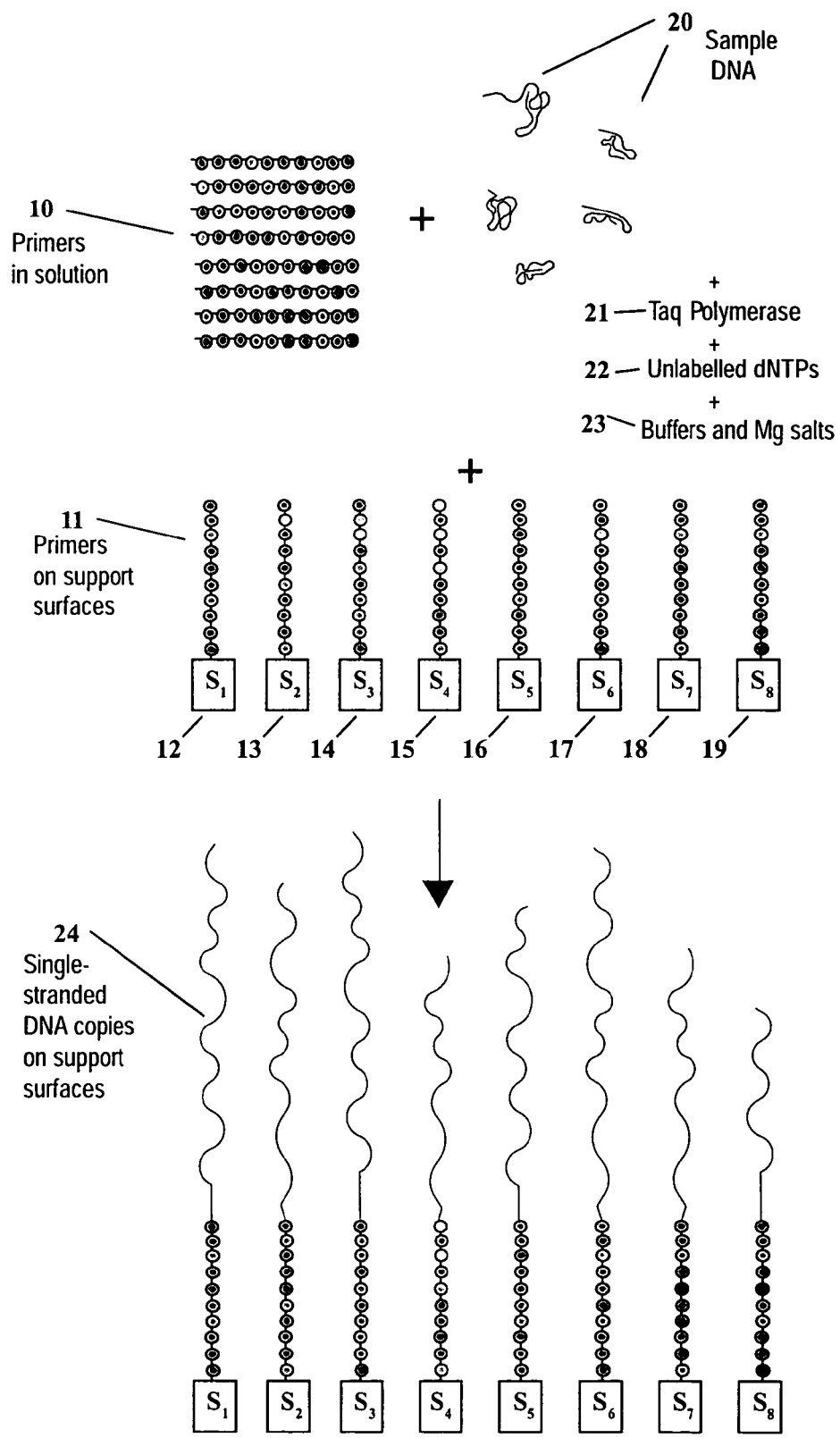
FIG. 4 shows schematically a process for performing PCR on multiple solid supports.

A preferred method of practising the invention is illustrated schematically in FIG. 4. According to this method, a set 10 of oligonucleotide primers in solution is used in conjunction with a set 11 of the same oligonucleotide primers each of which is attached to one of a set of individual support surfaces 12 to 19 inclusive. Each of the solid support surfaces may be a discrete entity, for example an RF tag as hereinbefore described and illustrated in FIG. 1, or may be a zone of a larger surface, for example the glass plate of FIG. 2 or the silicon wafer of FIG. 3. Other types of support surfaces suitable for the practice of the invention include glass or plastic beads labelled with uniquely-identifiable markers, such as defined-ratio combinations of fluorescent dyes or specific combinations of other molecules. Support media of these types are commercially available for applications in combinatorial chemistry and biochemical analysis.

In a first step of the method of this embodiment, the set 11 of oligonucleotide primers attached to the solid-support surfaces 12 to 19 inclusive is contacted with a solution containing a set 10 of the same oligonucleotide primers together with the sample 20 of double-stranded DNA molecules to be analysed, a polymerase enzyme 21, for example Taq DNA polymerase, a mixture 22 of unlabelled deoxynucleoside triphosphates comprising A-, G-, C- and T-deoxynucleoside triphosphates, and a mixture 23 of magnesium chloride and buffer salts, the solution being loaded into a sealable container which is adapted to contain all of the solid-support surfaces 12 to 19 inclusive. A wide variety of containers are suitable for the practice of the invention, for example microcentrifuge tubes may be used where RF tags are employed as solid-supports, or alternatively a sealable multi-well plate is also suitable. Where a single support surface subdivided into zones is used in the practice of the invention, sealable containers such as those employed for staining microscope slides may be employed. After physical division of such support surfaces, the individual zones may be transferred to microcentrifuge tubes for subsequent steps of the method of the invention.

Apparatus designed for combinatorial chemical synthesis may also be employed in practising the method of the invention. For example, reactor blocks containing multiple reaction chambers are suitable for use with RF tags or with individual zones of support surfaces after physical division of a single support surface subdivided into zones.

As will be understood by those skilled in the art of biochemical analysis, a wide variety of containers other than those mentioned here may also be employed in practising the method without departing from the spirit of the invention.

The sealed container is then loaded into a heating block or thermal cycler suitable for performing the Polymerase Chain Reaction (PCR) and subjected to multiple amplification cycles each comprising a denaturation step, an annealing step and an extension step. During each amplification cycle, segments of double-stranded DNA sequences in the sample to be analysed are amplified by PCR, the section of each such sequence amplified being determined by the presence and location of segments within each sequence possessing complementarity to one or more pairs of oligonucleotide primers.

After multiple cycles of amplification, the solution contains amplified copies of DNA segments contained within the sample to be analysed, formed by extension of members of the set 10 of oligonucleotide primers originally present in solution. In addition, the set 11 of solid-support-bound oligonucleotide primers also participates in the amplification process, so that each support surface also bears covalently-bound amplified copies of DNA segments contained within the sample to be analysed.

After completion of the PCR process, the solution is removed and the support surfaces are washed under denaturing conditions in order to remove all non-covalently-linked oligonucleotides and polynucleotides. After this operation, the set of solid-support surfaces carries a set 24 of single-stranded polynucleotides derived by amplification of molecules of the sample DNA 20 and covalently bound to the solid supports.

Figure 5:
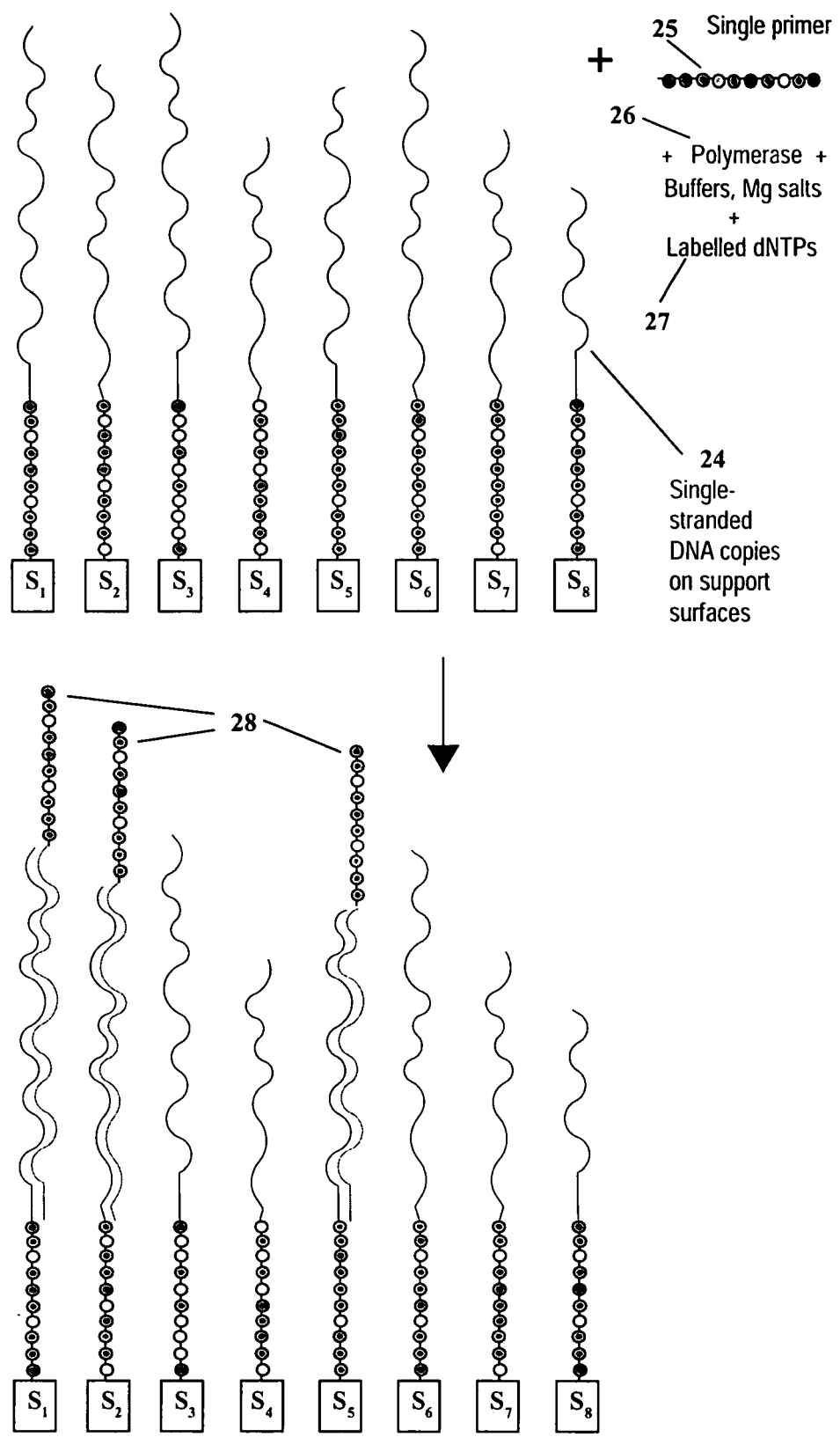
FIG. 5 shows schematically a process for generating labelled polynucleotides which are complementary to immobilised polynucleotides produced by PCR.

In a second step of the method of this embodiment, as illustrated schematically in FIG. 5, the set 24 of solid-support-bound single-stranded polynucleotides is subjected to a further primer-dependent polymerase reaction in which the sealable container accommodating the solid-supports is loaded with a solution containing a single oligonucleotide primer 25 which may be selected from the set 10 of oligonucleotide primers employed in the first step of the method. Alternatively, an unrelated oligonucleotide primer may be used. This oligonucleotide acts as a primer for synthesis of a complementary strand on each of the set 24 of solid-support-bound single-stranded polynucleotides. The solution also contains a polymerase enzyme 26, for example Taq DNA polymerase, together with magnesium chloride and buffer salts, and a mixture 27 of deoxy nucleoside triphosphates, comprising A-,G-,C- and T-deoxynucleoside triphosphates, together with a labelled molecule. The labelled molecule is one which may be incorporated into the complementary strand formed on each polynucleotide during the primer-dependent polymerase reaction. For example, a Uridine derivative such as biotin-16-dUTP or aminoallyl-dUTP may be included in the polymerase reaction mixture in order to incorporate biotin labelled molecules or aminoallyl substituents suitable for labelling in place of Thymidine units within the complementary strand during the primer-dependent polymerase reaction.

Figure 6:
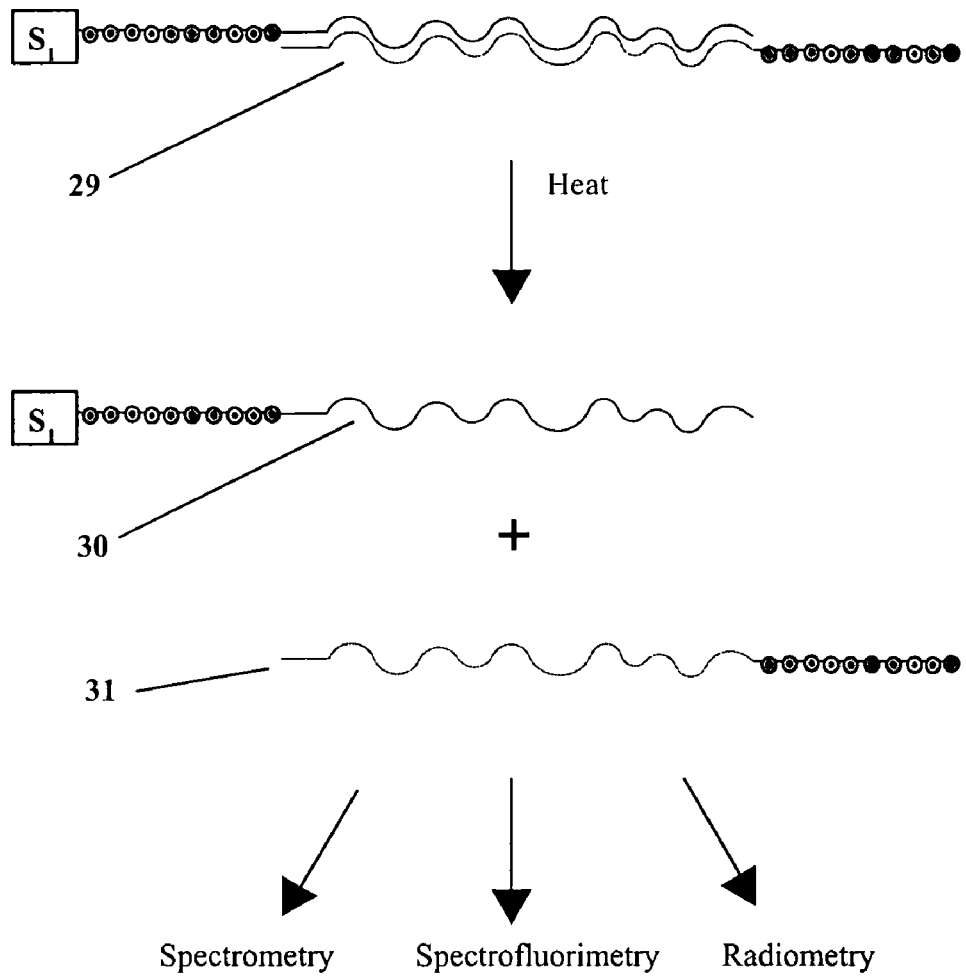
FIG. 6 shows schematically procedures for analysis of complementary polynucleotides.

Alternatively, the label may be attached to the 5'-terminus of the oligonucleotide primer, as is commonly employed in DNA sequencing. In this case fluorescent dyes such as those commonly known as FAM, JOE, TAMRA and ROX, which are commercially available from Applied Biosystems, may be incorporated into the oligonucleotide primer during synthesis. Similarly, a 5'-biotin label may be incorporated into the oligonucleotide during synthesis by use of a biotin phosphoramidite. Radioactive labels may also be used where appropriate. Where the label is attached to the oligonucleotide, the subsequent polymerase-mediated reaction may be omitted and replaced by a simple hybridisation process in which the labelled oligonucleotide serves as a probe for detection of complementary sequences contained in the solid-support-bound single-stranded polynucleotides. However, greater sensitivity may be obtained by incorporating multiple labels into the second strand by performing the polymerase reaction in the presence of labelled nucleotide triphosphates. Alternatively, different labels may be incorporated into the oligonucleotide primer and the nucleotide triphosphates, allowing determination of the ratio of 5'-terminal label to labels incorporated during second-strand synthesis. This may be used, for example, to obtain estimates of the chain length and base composition of the second strand. Where suitable detection means are available, multiple fluorescent dyes or other labels may be used for this purpose, such that each of the four nucleotide triphosphates contains a different dye, allowing the labels associated with each nucleotide to be determined separately. Where appropriate, multiple sets of reactions may be performed using the same combinations of oligonucleotides but with different labelled nucleotides in each reaction, providing further levels of nucleotide-specific information. The primer-dependent polymerase reaction may be driven to completion by subjecting the solution to thermal cycling as described in the foregoing description of the first step of the method of this embodiment. In this second step, however, the polymerisation products are formed in solution rather than on the solid-support surface, the set 24 of solid-support-bound single-stranded polynucleotides serving as the templates for second-strand synthesis. The resulting solution contains labelled polynucleotides complementary to the solid-support-bound polynucleotides which are then allowed to hybridise together to form double-stranded polynucleotides in which one strand is bound to the solid-support surface. After washing to remove unbound material, the quantity of label attached to each support surface is then determined using standard procedures for quantitation of fluorescent or luminescent molecules or, in the case of a radioactive label, radiometry or autoradiography. Where appropriate, support surfaces divided into zones such as those illustrated in FIG. 2 and FIG. 3 may first be physically divided before quantitation of the labelled molecules attached to each zone. The divided zones may then be quantitated individually, for example by elution of the labelled molecule prior to spectrophotometric, spectrofluorimetric or radiometric determination of the eluate. The process of elution and quantitation is illustrated schematically in FIG. 6, in which a double-stranded polynucleotide 29 attached to an individual support zone is heated in an appropriate buffer solution in order to dissociate the polynucleotide into a single-stranded support-bound polynucleotide 30 and the labelled complementary strand 31, which is released into solution. After removal of the solid support, the concentration in solution of the labelled molecules is determined by spectrometry, spectrofluorimetry or radiometry as appropriate. As will be apparent to those skilled in the art of DNA sequence analysis, the method of the invention as described above may be modified in a variety of ways without departing from the spirit of the invention. For example, the set of solid-support-bound polynucleotides produced in the first step of the method may be applied directly in other techniques for which such supported molecules are employed, as in the preparation and application of DNA micro-arrays for detection of genetic sequences by hybridisation. Similarly, the amplification of genetic sequence information from sample molecules by PCR may be performed in two stages, using only the solution-phase primers initially in order to obtain a preliminary degree of amplification before introducing the solid-supported primers. Where appropriate, a purification or concentration step may be included after such initial amplification in order to remove residual sample DNA or selectively carry forward specific amplification products for incorporation into the solid-support-bound polynucleotides by further cycles of PCR. Similarly, other detection strategies may be adopted in order to eliminate the requirement for labelling, for example by using mass-spectrometric or electrochemical techniques to characterise the polynucleotides produced.

Figure 7:
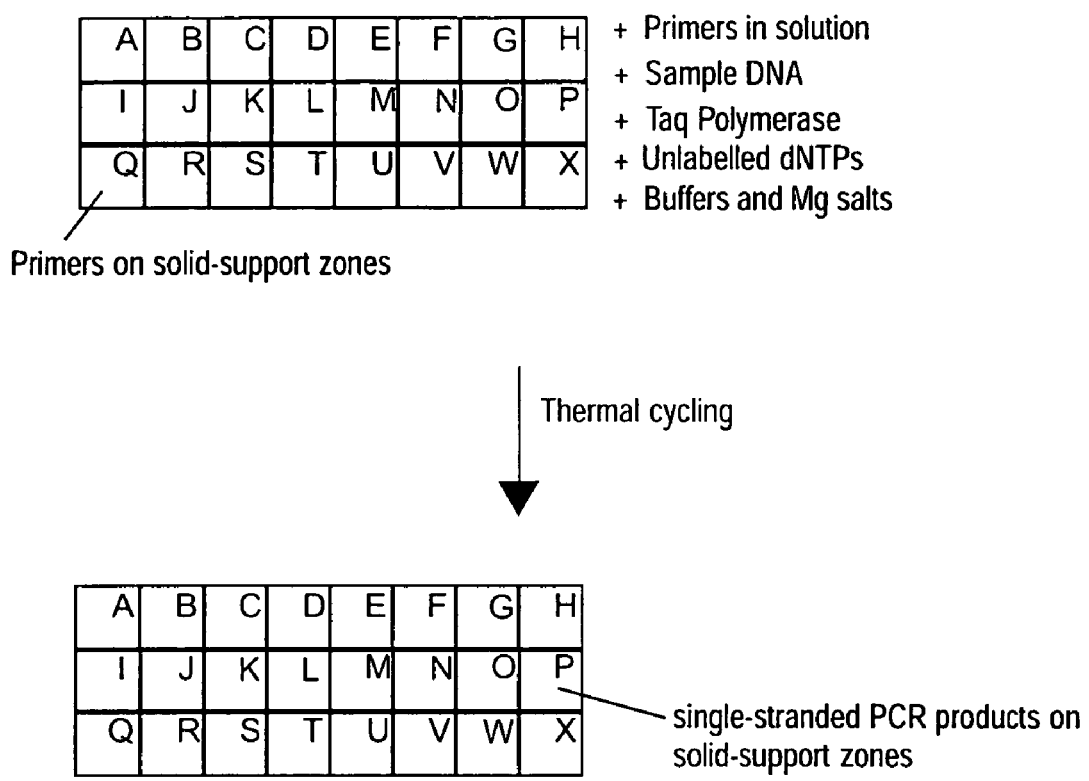
FIG. 7 shows schematically a process for performing PCR on a single solid support subdivided into zones.
Figure 8:
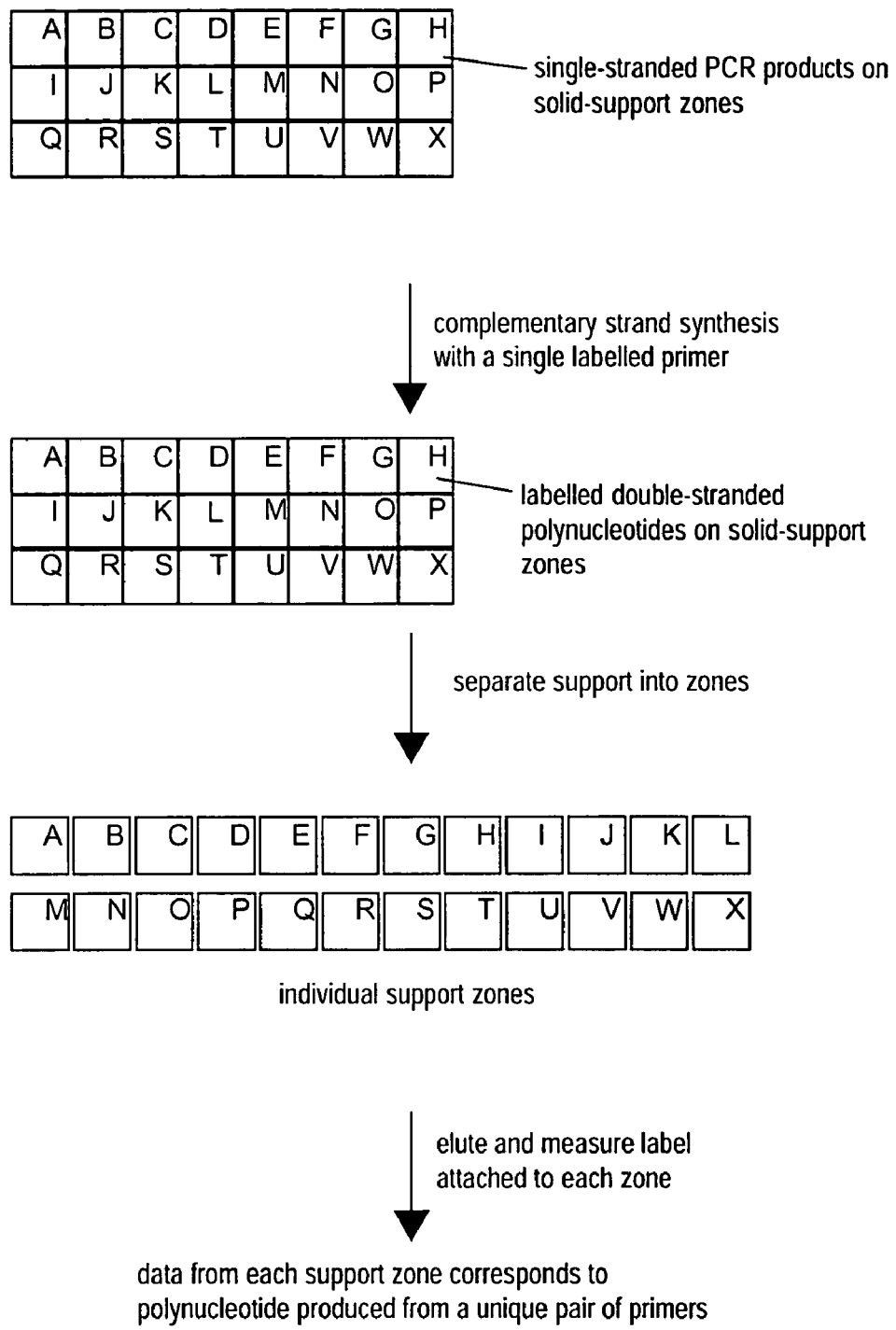
FIG. 8 shows schematically a process for generating labelled complementary sequences after separating a single solid support into individual zones.

The method of the invention as applied to a single support surface divided into support zones is further illustrated schematically in FIG. 7, which summarises the steps involved in production of single-stranded PCR products attached to the solid-support zones and in FIG. 8, which summarises the subsequent operations of complementary strand synthesis, separation of the support into individual zones, and elution and quantitation of labelled complementary strands.

Alternatively, each zone of the surface may be quantitated individually without physical division of the support surface where an appropriate instrumental technique for doing so is available, for example by use of a laser scanner where fluorescently-labelled molecules are to be determined. Individual support surfaces are identified by reading the identification means from each surface, whether these be attached or engraved indicia as in the surface zones of FIG. 2 and FIG. 3 or coded RF tags as in FIG. 1.

Since the sequence of the 5'-terminus of each solid-support-bound polynucleotide is known from the sequence of the oligonucleotide initially applied to that support surface, and the sequence of the 3'-terminus of each solid-support-bound polynucleotide is known to be complementary to the single primer oligonucleotide present in solution in the second step of the method, the results from all support surfaces may be used to deduce sequence information for the sample to be analysed. For example, the sequences of the primer oligonucleotides may be selected so as to demonstrate the presence or absence of a specific polynucleotide in the analyte which is associated with a microbial infection or other disease condition or of a genetic disorder.

The second step of the method may be repeated using the same set of support-bound polynucleotides with a different primer oligonucleotide in solution in order to obtain further sequence information. This procedure may be applied iteratively so as to examine all possible combinations of the chosen set of primer oligonucleotides. In the example illustrated schematically in FIG. 4, where a set of eight primer oligonucleotides is employed, there are 64 possible combinations of the primer oligonucleotides which may be examined in this manner.

A particular advantage of the process of this embodiment is that it has the capacity to provide verification of results, since, if double-stranded template DNA is being analysed, each of the possible pairs of oligonucleotides should produce two signals, one for the combination of a solid-support-bound primer $P_1$ with a solution-phase primer $P_2$, and a corresponding signal for the complementary strand represented by the combination of solid-support-bound primer $P_2$ with solution-phase primer $P_1$.

As will be appreciated by those skilled in the art of DNA analysis and combinatorial chemistry, much larger sets of primer oligonucleotides than those depicted in this figurative example may be employed in order to generate results from hundreds or thousands of combinations of the primer oligonucleotides.

Figure 9:
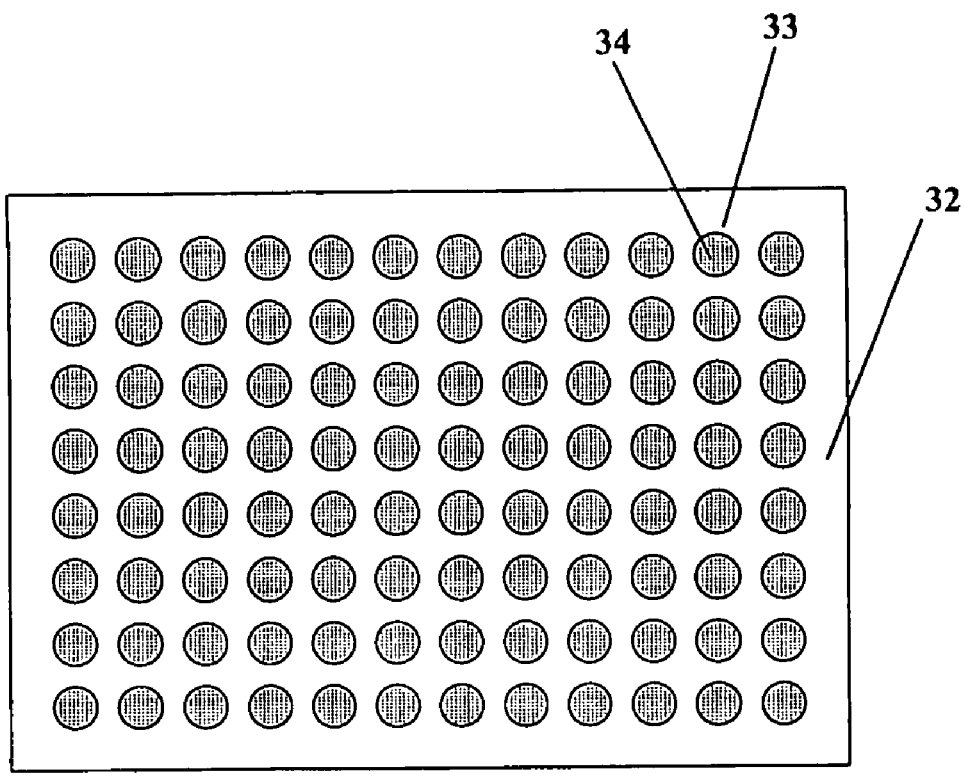
FIG. 9 shows, in plan view, a 96-well plate in which each well contains an oligonucleotide array.
Figure 10:
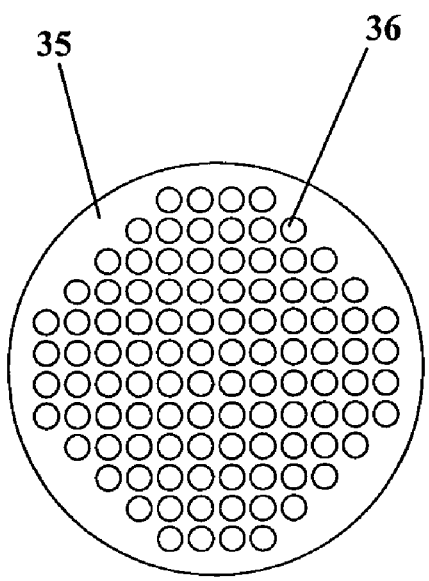
FIG. 10 shows, in plan view, an individual oligonucleotide array.

A fourth preferred embodiment of the apparatus of the invention comprises an apparatus for analysis of DNA samples using a set of 96 primer oligonucleotides, as illustrated in FIG. 9. In this embodiment, the support surface is formed into wells, the base of each well being planar and bearing an array of oligonucleotides. Referring to the drawings, FIG. 9 shows in plan view a 96-well plate 32 in which each well 33 contains an array 34 of oligonucleotides. A detailed plan view of an individual array is shown in FIG. 10, in which the circular base 35 carries multiple sub-zones 36 to each of which is attached an oligonucleotide. Each oligonucleotide is attached to the surface by means of a stable linker moiety covalently linked to the 5'-terminus of the oligonucleotide and covalently linked to the support surface. The stable linker moiety should be thermally stable in aqueous solution at 95 deg.C and hydrolytically stable between pH 4 and pH 11, allowing the linkage of oligonucleotide to the surface to withstand the conditions normally employed in practising techniques such as the polymerase chain reaction (PCR). The linker moiety may incorporate spacer molecules as part of the covalent linkage between oligonucleotide and support surface, in order to reduce or eliminate steric effects which may inhibit processes involving the oligonucleotides, for example binding of oligonucleotides to an enzyme molecule.

The identity of the oligonucleotide attached to each position of the array is established at the time of manufacture, so that individual identification means for each oligonucleotide are not required, the position of the oligonucleotide within the array serving to identify it uniquely. Additional positions may be included in each array to provide loci for placement of control substances and index markers for calibration and alignment purposes, especially where automated systems are to be used in quantitation and data acquisition. This is exemplified in FIG. 10, which contains eight additional sub-zones 35 in addition to the ninety-six zones required for placement of oligonucleotides.

The attachment of oligonucleotides to the planar base of each well may be performed directly on the material of the 96-well plate, for example by attaching suitable linker molecules to a polystyrene or polypropylene surface as described, for example, in the above-referenced U.S. Pat. No. 5,656,462 and WO 9932654. For ease of manufacture, however, it is preferable to attach the oligonucleotides to a planar slice of support material which may then be inserted into the base of each well. This permits the mass-production of the body of the 96-well plate from plastic materials suitable for use in an injection-moulding process while allowing other materials to be used as the support surface for the array which may then be fixed in position by an interference fit or by welding or using a suitable adhesive. Preferred materials for the planar slice are glass or a silicon oxide layer formed on a silicon wafer, and the slice may be of any suitable shape, for example circular, square, rectangular or hexagonal in form.

Figure 11:
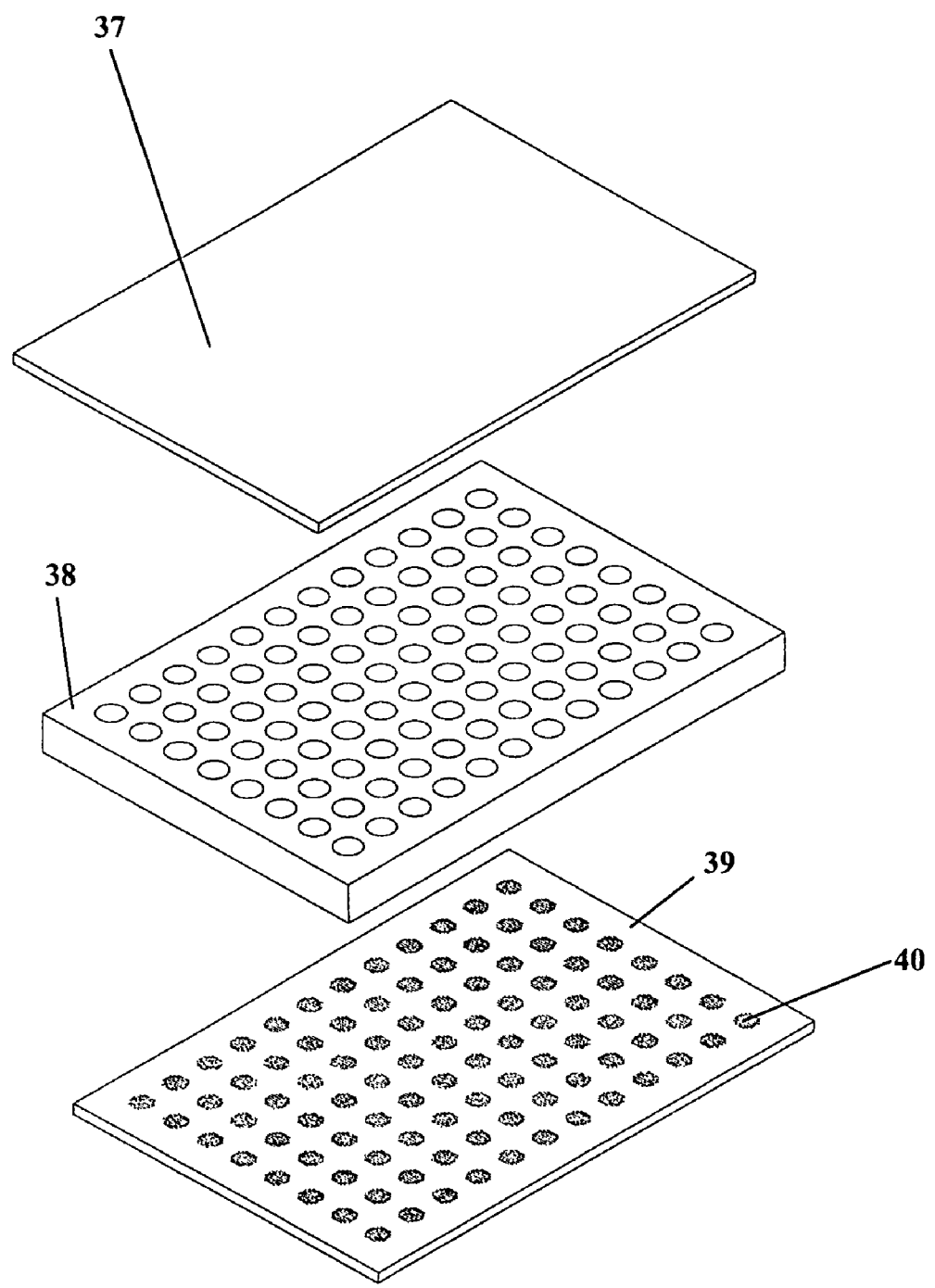
FIG. 11 shows, in exploded view, the components of a modular 96-well plate.
Figure 12:
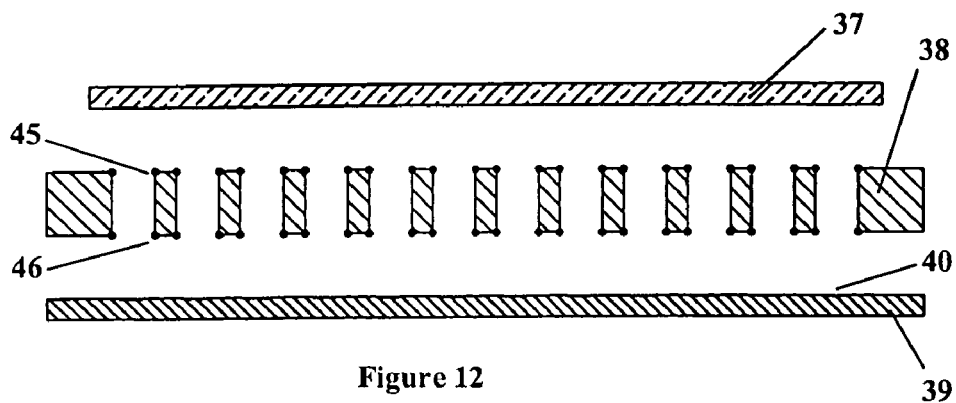
FIGS. 12 to 15 show, in sectional view, the assembly of the components of a modular 96-well plate mounted between heating blocks.

In a fifth preferred embodiment of the apparatus of the invention, a 96-well plate of modular construction is provided. This has three major components: a cover plate, a body divided into 96 cylindrical compartments opening on to both faces of the body, and a baseplate carrying 96 oligonucleotide arrays. These components may be combined to form a stack as illustrated in FIG. 11, in which the cover plate 37 overlies the body section 38, which in turn is placed over the baseplate 39 carrying the arrays 40. The assembly of the stack is shown in sectional view in FIG. 12, in which the cover plate 37 overlies the body section 38, which in turn is placed over the baseplate 39 carrying the arrays 40. O-ring seals 45 and 46 are fitted to the upper and lower ends of each of the cylindrical bores in the body component to form a fluid-tight seal against the cover plate and the baseplate.

Figure 13:
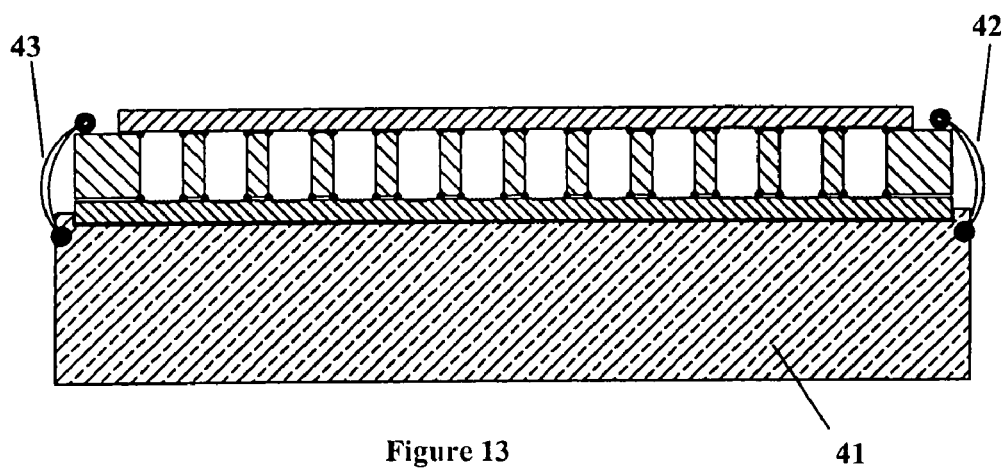
Figure 14:
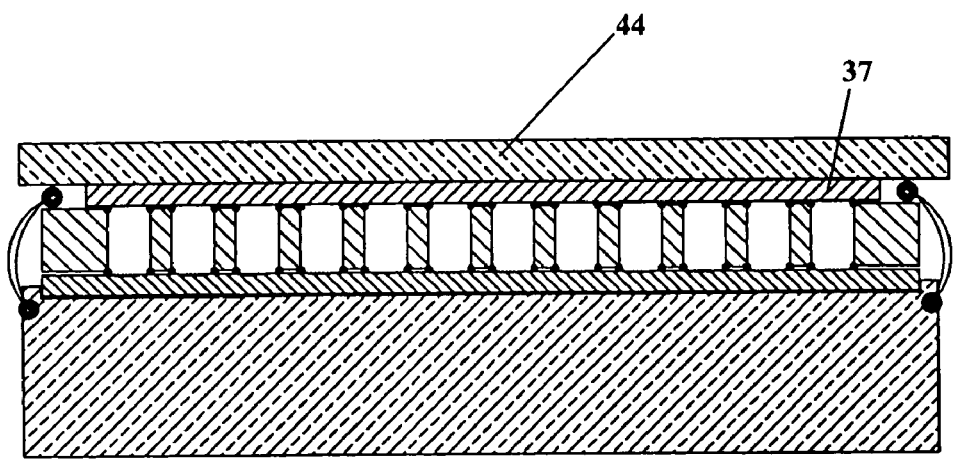
Figure 15:
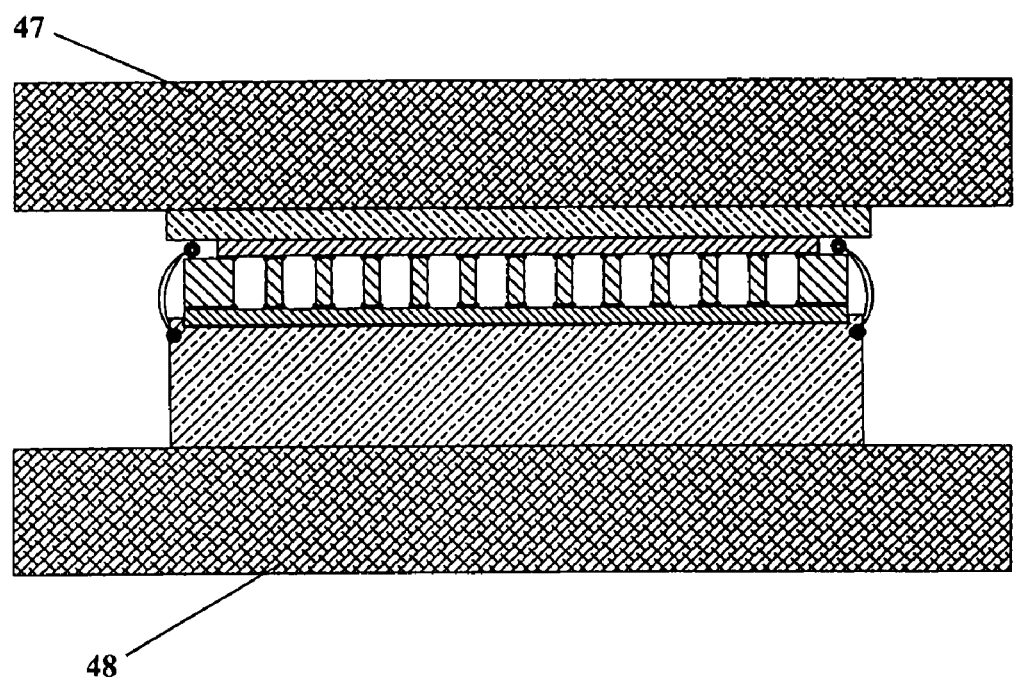

In use, as illustrated in FIG. 13, the baseplate and body are fitted to a metal base 41 and held in place by spring clips 42 and 43. At this stage, each well is sealed at its lower end against the baseplate and may be charged with solutions appropriate to the analysis to be performed. Following this, as illustrated in FIG. 14, the cover plate 37 may be placed in position and held in place by a metal pressure plate 44. This serves to seal the upper end of each well against the cover plate. As illustrated in FIG. 15, where thermal cycling is required, for example in order to perform polymerase chain reactions on the arrays, the entire assembly may now be compressed between two heated metal plates 47 and 48, the upper plate serving to prevent condensation on the underside of the cover plate. Where "hot start" conditions are required, the metal base 41 may be placed on a heated surface prior to loading solutions in the wells, following which the cover plate 37 and pressure plate 44 may be fitted.

Figure 16:
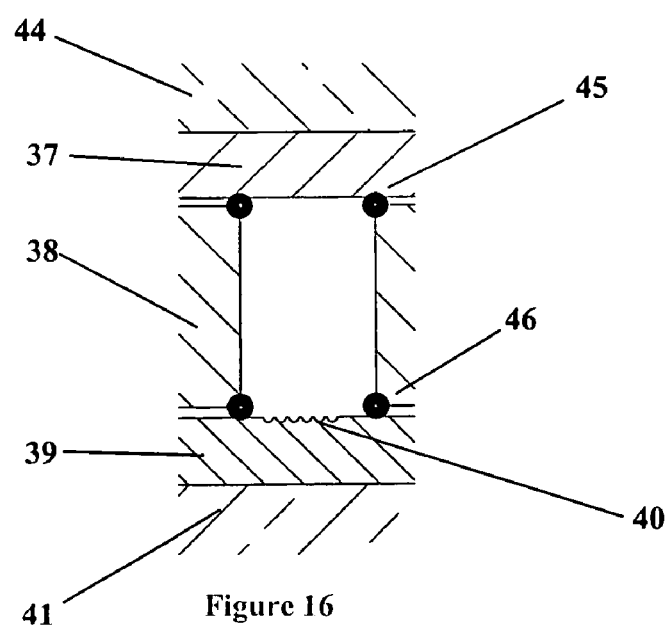
FIG. 16 shows, in sectional view, the detailed construction of an individual well of a 96-well plate.

The internal arrangement of an individual well of the assembled apparatus is illustrated in FIG. 16, in which the baseplate 39 bearing the oligonucleotide array 40 is supported on metal base 41, the cylindrical bore of the body component 38 is sealed against the baseplate by O-ring seal 46 and by O-ring seal 45 against the cover plate 37 which is held in place by pressure plate 44.

Where, as hereinbefore described, the process of the invention is to be performed using an initial amplification step using only solution-phase primers before introducing the solid-support bound primers, this may be accomplished simply by initially inverting the apparatus during the first step of the process, so that the baseplate 39 bearing the oligonucleotide arrays is uppermost. In this configuration, the solution in each well is not in contact with the solid-support bound oligonucleotides of the array surfaces, and PCR proceeds using only solution-phase primers. After the initial amplification step, the apparatus is inverted again, allowing the solid-support bound primers to participate in subsequent cycles of PCR amplification. Preferred materials for the construction of the metal base 41 and pressure plate 44 are aluminium or stainless steel. Preferred materials for the construction of the body 38 and cover plate 37 are polypropylene, polytetrafluorethylene (PTFE), polyether ether ketone (PEEK) or polystyrene. A preferred material for the construction of the baseplate 39 is glass. Preferred materials for the O-ring seals are fluorocarbon rubber or EPDM.

The arrays 40 may be formed directly on the surface of the baseplate 39 using a commercial robotic arraying system. Alternatively, the arrays may be manufactured individually on plates of glass or surface-oxidised silicon wafers as hereinbefore described and fixed to the baseplate 39 by welding or by using a suitable adhesive, in which case the baseplate may be manufactured from a plastic material such as polypropylene or polystyrene. The plates carrying the arrays may be disc-shaped, as depicted in FIG. 10, or may equally be rectangular, square or hexagonal in form. Where silicon wafers are used for construction of arrays, a square or rectangular form may be preferred to facilitate handling of diced wafer sections by use of standard microfabrication and handling equipment.

This embodiment of the apparatus of the invention allows all possible combinations of 96 oligonucleotides to be generated in a single analysis. By analysing the results from multiple experiments, information may be deduced as to the sequence of DNA molecules of the sample, particularly by using appropriate computer programs to interpret the data generated. The 96-well layout may be further extended to encompass 384-well or 1536-well formats, enabling many more combinations of primers to be generated.

A particularly useful aspect of the procedures of the invention is the ability to discriminate between populations of DNA molecules even where little is known about the genetic sequences involved. This can be achieved by choosing primers from sets of oligonucleotides which are selected randomly, with the proviso that their (G+C) content should be between 60% and 70% and that they should not have self-complementary ends. These criteria ensure that the oligonucleotides will prime efficiently during the PCR process. Such random sets of oligonucleotides are commonly used in the technique of Random Amplified Polymorphic DNA (RAPD) production by PCR, and are commercially available. Examples of typical 10-base primer sets are given in FIG. 17. The nucleotide sequences given in this diagram are for illustrative purposes only and do not represent the sequences of actual biological materials.

In a second preferred embodiment of the process of the invention, individual support surfaces are functionalised with a mixture of two or more oligonucleotides in combination prior to practising the method hereinbefore described. This allows results to be obtained for one or more sub-sets of the set of oligonucleotides. This may be useful, for example, as a preliminary screening method prior to refining the method in subsequent experiments by using individual support-bound oligonucleotides as in the hereinbefore-described method.

In a third preferred embodiment of the process of the invention, the solution used during the second step of the method, in which complementary strand synthesis is performed, contains a mixture of two or more oligonucleotides in combination. The method is otherwise practised as hereinbefore described. This allows results to be obtained for one or more sub-sets of the set of oligonucleotides. This may be useful, for example, as a preliminary screening method prior to refining the method in subsequent experiments by using individual support-bound oligonucleotides as in the hereinbefore-described method.

In a fourth preferred embodiment of the process of the invention, individual support surfaces are functionalised with a mixture of two or more oligonucleotides in combination and the solution used during the second step of the method, in which complementary strand synthesis is performed, contains a mixture of two or more oligonucleotides in combination. The method is otherwise practised as hereinbefore described. This allows results to be obtained for one or more sub-sets of the set of oligonucleotides. This may be useful, for example, as a preliminary screening method prior to refining the method in subsequent experiments by using individual support-bound oligonucleotides as in the hereinbefore-described method.

In a fifth preferred embodiment of the process of the invention, solutions of two or more different oligonucleotides are applied separately to individual solid-supports or solid-support zones during the second step of the method, in which complementary strand synthesis is performed. The method is otherwise practised as hereinbefore described. This requires separate containment means for the individual solid-supports or solid-support zones. Where the individual solid-supports are separate entities, for example RF tags as illustrated in FIG. 1, or a single support surface which has been physically divided into individual support zones as hereinbefore described, this may be accomplished by placing each support entity in a separate tube or other container prior to performing the second step of the method as hereinbefore described. In the case of a single support surface subdivided into zones which have not been physically divided, this may be accomplished by applying a suitable gasket to the support surface to allow different solutions to be applied to each zone without cross-contamination.

In a sixth preferred embodiment of the process of the invention, solutions of two or more different DNA samples are applied separately to individual solid-supports or solid-support zones during the first step of the method, in which PCR amplification products are formed on the solid-supports.

The method is otherwise practised as hereinbefore described. This requires separate containment means for the individual solid-supports or solid-support zones. Where the individual solid-supports are separate entities, for example RF tags as illustrated in FIG. 1, this may be accomplished by placing each support in a separate tube or other container prior to performing the method as hereinbefore described. In the case of a single support surface subdivided into zones, this may be accomplished by applying a suitable gasket to the support surface to allow different solutions to be applied to each zone without cross-contamination.

In a seventh preferred embodiment of the process of the invention, solutions of labelled complementary strands eluted from one support surface are applied to another support surface and allowed to hybridise thereto. Following this operation, the support surface is washed to remove unbound material and hybridised polynucleotide is eluted by washing under more stringent conditions and quantitated by the appropriate method. This procedure may be repeated for all possible combinations of such eluted complementary strands and support surfaces and the data thereby obtained applied in various ways, for example in the construction of a linkage map for the DNA sample of the analyte.

As will be apparent to those skilled in the arts of biochemical analysis and DNA technology, a large number of different combinations of oligonucleotides may be selected from the total number of possible oligonucleotides of any given chain-length, and each combination will give different results for any given sample of DNA which may be subjected to analysis by practising the invention. Very large volumes of data may therefore be generated by performing multiple analyses of a sample using different combinations of oligonucleotides in each case. As will also be apparent to those skilled in the art of biochemical analysis, the statistical probability of finding a match between any given oligonucleotide and a sub-sequence of a component DNA molecule within a given sample is a function of the length of the oligonucleotide, and this parameter may be varied as required in order to obtain informative results from the methods of the invention.

A particular advantage of the technique of the invention is the statistical improbability of a particular combination of two sub-sequences occurring more than once in a given population of DNA molecules. This is in contrast to the relatively high probability of random occurrences of a single sub-sequence in a given population of DNA molecules. Taking the example of a sub-sequence composed of 10 nucleotides, the total possible number of such sequences is approximately 1 million. This is a relatively small number in relation to the size of the human genome, for example, which contains three thousand million base-pairs. Random occurrences of a particular 10 nucleotide sequence might therefore be expected to occur relatively frequently within the human genome. In contrast, the number of possible combinations of two different 10-nucleotide sequences is approximately five hundred million million million. This number is much larger than the number of base-pairs in the human genome, and the chances of a particular combination of two 10-nucleotide sequences occurring more than once in the population of DNA molecules comprising the human genome are correspondingly reduced.

The technique of the invention may therefore be used to implement highly-specific DNA-based detection procedures for a particular genetic material with a low probability of obtaining spurious results due to the random occurrence of matching DNA sequences in the sample.

An example of the application of the process of the invention to discriminate between two different DNA molecules is illustrated in FIG. 18. The nucleotide sequences given in this diagram are for illustrative purposes only and do not represent the sequences of actual biological materials.

Referring to the diagram, if it is desired to discriminate between the two double-stranded 100-base-pair DNA sequences, sequence X and sequence Y, this may be achieved using a set of oligonucleotide primers of appropriate sequence. The diagram illustrates a set of eight 15-base oligonucleotide primers A to H inclusive. The 8×8 matrix tables in the lower part of the diagram represent the results which would be obtained by application of the process of the invention using this set of primers and the two DNA sample molecules X and Y. In each table, the columns represent the oligonucleotides attached to the solid-support during the first step of the process, in which sequence information from the sample molecules is transcribed into solid-supported primer-extension product. Conversely, the rows of each table represent the solution-phase oligonucleotides used during the second step of the process, during which labelled second-strands complementary to the support-bound polynucleotides are produced. The presence of a "+" symbol in each table indicates a combination which gives rise to incorporation of labelled molecules into the product, whereas the presence of a "−" symbol denotes the absence of labelled molecules.

As indicated by the sections highlighted in bold type, sequence X contains two sequences of nucleotides which match those of two of the eight primers. A match for primer C is found in the "top" strand of sequence X, reading from left to right, while a match for primer B is found in the "bottom" strand, in which the 5'-terminus is at the right-hand end, and the sequence therefore reads from right to left. Reference to the matrix table for sequence X shows that a positive result is obtained for this combination of primers, which may be generated in two different ways, depending on which of the two primers is attached to the solid support. Similarly, sequence Y contains matching sequences for primer A in the "top" strand, reading from left to right, and for primer H in the "bottom" strand, reading from right to left. Reference to the matrix table for sequence Y again shows that a positive result is obtained for both of the ways in which this combination of primers may be generated.

As will be apparent to those skilled in the art of electronic logic circuitry, the matrix tables shown in the figure are analogous to the "truth tables" used in analysis of semiconductor logic devices, and the process of the invention may be regarded as providing the functionality of an "AND" logic gate for DNA sequences. As such, the outcome of a particular experiment may be predicted in advance if the nucleotide sequences of the sample molecules and the primers are known, allowing analytical procedures for specific applications to be designed "in-silico", using computer modelling techniques.

As will be appreciated by those skilled in the art of DNA analysis and combinatorial chemistry, the operations involved in practising the methods of the invention may readily be automated by using standard items of laboratory equipment designed for use in combinatorial chemical synthesis and high-throughput screening. These may include but are not restricted to thermal cyclers, automated pipettors, diluters and dispensers, robotic systems, two-dimensional (X-Y) positioning systems and three-dimensional (X-Y-Z) motion systems, multi-tube racks, multi-compartment reaction blocks and multi-well plate systems, plate readers, autosampling apparatus, spectrophotometers and spectrofluorimeters including flow-through spectrophotometers and spectrofluorimeters. In addition, equipment designed for specific applications in oligonucleotide synthesis may also be adapted for the practice of the invention. Such equipment may include but is not restricted to automated synthesisers such as those described in my U.S. Pat. No. 4,728,502 entitled "Apparatus for the chemical synthesis of oligonucleotides" and in my GB patent 2,347,141 entitled "Combinatorial synthesiser".

The foregoing description illustrates embodiments of the invention. However, the invention is not restricted to the specific embodiments described, and many variations of the invention will be apparent to those skilled in the arts of biochemical analysis and DNA technology without departing from the spirit of the invention. For example, a wide variety of enzymes and enzymatic processes could be used in the practice of the invention in place of the polymerase chain reaction, including reverse transcriptase in order to practise the technique of RT-PCR, or DNA ligase in order to practise the ligase chain reaction.

Similarly, although the subdivided support surfaces hereinbefore described are arranged in a rectangular format, other formats, for example formats employing a hexagonal or triangular layout of sub-zones, would be equally effective.

Accordingly, the scope of the invention should not be determined by reference to the foregoing description, but solely by reference to the appended claims along with their full scope of equivalents.

The invention claimed is:

1. A process for the analysis of a nucleic acid sample so as to determine the simultaneous presence in the sample of two or more target sequences each bounded by first and second oligonucleotide primer sequences, said process comprising the steps of:
  (i) providing a first multiplicity of different oligonucleotide primers, each covalently anchored at its 5'-terminus to a discrete, individually identifiable, solid support surface, wherein the first multiplicity comprises the first and second oligonucleotide primer sequences,
  (ii) providing a second multiplicity of oligonucleotide primers, in solution, wherein the nucleotide sequences of respective members of said first and second oligonucleotide primer multiplicities are identical to each other,
  (iii) performing a polymerase chain reaction amplification on said sample in the presence of both said first and second oligonucleotide primer multiplicities, so as to convert said anchored oligonucleotide primers to anchored polynucleotide chain extension products,
  (iv) separating said solid support surface anchored polynucleotide chain extension products from the resulting solution, and
  (v) determining, for each said separated solid support-linked chain extension product, which of said second multiplicity of oligonucleotide primers is a complementary sequence to a portion of a said chain extension product, whereby the presence of the two or more target sequences is detected in the sample.

2. The process of claim 1 wherein the determination of which of said second multiplicity of oligonucleotide primers is a complementary sequence to a portion of said anchored chain extension product is performed by probing serially with different labelled oligonucleotides, each having a sequence corresponding to that of a respective one of said second multiplicity of oligonucleotide primers, with removal of any bound labeled oligonucleotide after each probing step.

3. The process of claim 1 wherein the determination of which of said second multiplicity of oligonucleotide primers is a complementary sequence to a portion of said anchored chain extension product is effected by a serial multiple probing process using primer-directed complementary strand synthesis with different oligonucleotide primers, each having a sequence corresponding to that of one of said second multiplicity of oligonucleotide primers together with labeled nucleotide monomers, with removal of any bound complementary strand after each probing step.

4. The process of claim 1, wherein the solid support surface comprises a multiplicity of solid support zones, each solid support zone comprising the first multiplicity of anchored oligonucleotides, which solid support zones are processable separately from each other, such that all possible combinations of primers may be utilized in a single analysis, and wherein the determination of which of said second multiplicity of oligonucleotide primers is a complementary sequence to a portion of said solid support-linked chain extension product is effected by a parallel multiple probing at each one of said multiplicity of solid support zones with different labeled oligonucleotides for each of said multiplicity of solid support zones, each having a sequence corresponding to that of a respective one of said second multiplicity of oligonucleotide primers.

5. The process of claim 1, wherein the solid support surface comprises a multiplicity of solid support zones, each solid support zone comprising the first multiplicity of anchored oligonucleotides, which solid support zones are processable separately from each other, such that all possible combinations of primers may be utilized in a single analysis, and wherein the determination of which of said second multiplicity of oligonucleotide primers is a complementary sequence to a portion of said solid support-linked chain extension product is effected by a parallel multiple probing process at each one of said multiplicity of solid support zones using primer-directed complementary strand synthesis with a third multiplicity of oligonucleotide primers being used for each of said multiplicity of solid support zones, each having a sequence corresponding to that of one of said second multiplicity of oligonucleotide primers, together with labeled nucleotide monomers.

6. The process of claim 1 wherein the solid support-anchored oligonucleotide primers are anchored to discrete solid support surfaces provided in a microarray device.

7. The process of claim 1 wherein the solid support-anchored oligonucleotide primers are anchored to discrete solid support surfaces provided on respective beads bearing identification indicia.

8. The process of claim 1 wherein the oligonucleotide primers contain internucleotide linkages selected from phosphodiesters, phosphorothioates and methyl phosphonates.

9. The process of claim 1 wherein the nucleic acid analyte is selected from single-stranded DNA, double-stranded DNA, and messenger RNA.

10. A process for the analysis of a nucleic acid sample so as to determine the simultaneous presence in the sample of two or more target sequences each bounded by first and second oligonucleotide primer sequences, said process comprising the steps of:
   (i) providing a first multiplicity of different oligonucleotide primers, each adapted for covalently anchoring at its 5'-terminus to a solid support surface, wherein the first multiplicity comprises the first and second oligonucleotide primer sequences,
   (ii) providing a second multiplicity of oligonucleotide primers, in solution, wherein the nucleotide sequences of respective members of said first and second oligonucleotide primer multiplicities are identical to each other,
   (iii) providing a solid support surface comprising a multiplicity of individually identifiable support zones, every one of which is subdivided into discrete, individually identifiable loci,
   (iv) covalently anchoring each member of the first multiplicity of oligonucleotide primers to an individually identifiable locus of each individually identifiable support zone,
   (v) for every individually identifiable support zone comprising said first multiplicity of anchored oligonucleotide primers, performing a polymerase chain reaction amplification on said sample in the presence of said second multiplicity of oligonucleotide primers, so as to convert said anchored oligonucleotide primers to anchored polynucleotide chain extension products,
   (vi) separating said solid support surface covalently anchored polynucleotide chain extension products from the resulting solutions, and
   (vii) determining, for each said covalently anchored chain extension product, which of said second multiplicity of oligonucleotide primers is a complementary sequence to a portion of said chain extension product,
   whereby amplification products from all possible combinations of primers are generated in a single analysis, and the presence of the two or more target sequences is detected in the sample.

11. The process of claim 10 wherein the determination of which of said second multiplicity of oligonucleotide primers is a complementary sequence to a portion of said covalently anchored chain extension products is performed by probing with a different labeled oligonucleotide for each of said individually identifiable support zones, each labeled oligonucleotide having a sequence corresponding to that of a respective one of said second multiplicity of oligonucleotide primers.

12. The process of claim 10, wherein the determination of which of said second multiplicity of oligonucleotide primers is a complementary sequence to a portion of said covalently anchored chain extension products is effected by a parallel multiple probing process at each one of said individually identifiable zones using primer-directed complementary strand synthesis with a third multiplicity of oligonucleotide primers, a different primer from said third multiplicity of oligonucleotide primers being used for each of said multiplicity of individually identifiable support zones, each having a sequence corresponding to that of one of said second multiplicity of oligonucleotide primers, together with labeled nucleotide monomers.

* * * * *